United States Patent
Lewis et al.

(10) Patent No.: US 7,429,672 B2
(45) Date of Patent: Sep. 30, 2008

(54) PROCESS FOR THE DIRECT SYNTHESIS OF TRIALKOXYSILANE

(75) Inventors: Kenrick M. Lewis, Flushing, NY (US); Rudolph A. Cameron, Bensalem, PA (US); James S. Ritscher, deceased, late of Cody WY (US); by Karen Ritscher, legal representative, Cody, WY (US)

(73) Assignee: Momentive Performance Materials Inc., Wilton, CT (US)

( * ) Notice: Subject to any disclaimer, the term of this patent is extended or adjusted under 35 U.S.C. 154(b) by 45 days.

(21) Appl. No.: 11/450,538

(22) Filed: Jun. 9, 2006

(65) Prior Publication Data

US 2007/0287850 A1    Dec. 13, 2007

(51) Int. Cl.
C07F 7/08 (2006.01)
C07F 7/18 (2006.01)
(52) U.S. Cl. .................................. 556/470; 556/472
(58) Field of Classification Search ............... 556/470, 556/472
See application file for complete search history.

(56) References Cited

U.S. PATENT DOCUMENTS

| | | | |
|---|---|---|---|
| 494,837 A | 4/1893 | Bellamy | |
| 893,448 A | 7/1908 | Covert | |
| 3,325,529 A * | 6/1967 | Greene, et al. | 558/356 |
| 3,343,406 A | 9/1967 | Branger | |
| 3,403,091 A | 9/1968 | Currey et al. | |
| 3,641,077 A | 2/1972 | Rochow | |
| 3,775,457 A | 11/1973 | Muraoka et al. | |
| 3,809,548 A | 5/1974 | Aas et al. | |
| 4,328,175 A | 5/1982 | Roeckel et al. | |
| 4,450,282 A | 5/1984 | Ritzer et al. | |
| 4,539,194 A | 9/1985 | Halvorsen | |
| 4,727,173 A | 2/1988 | Mendicino | |
| 4,761,492 A | 8/1988 | Childress et al. | |
| 4,762,939 A | 8/1988 | Mendicino | |
| 4,999,446 A | 3/1991 | Moody et al. | |
| 5,015,751 A | 5/1991 | Feldner et al. | |
| 5,059,343 A | 10/1991 | Halm et al. | |
| 5,084,590 A * | 1/1992 | Ritscher et al. | 556/470 |
| 5,094,832 A | 3/1992 | Forwald et al. | |
| 5,128,116 A | 7/1992 | Forwald et al. | |
| 5,166,384 A | 11/1992 | Bailey et al. | |
| 5,258,053 A | 11/1993 | Forwald et al. | |

(Continued)

FOREIGN PATENT DOCUMENTS

DE    83016 A    5/1970

(Continued)

OTHER PUBLICATIONS

Dhas et al. (1998) "Synthesis, Characterization and Properties of Metallic Copper Nanoparticles" *Chem Mater*, 10 p. 1446-1452.

(Continued)

*Primary Examiner*—Yvonne Eyler
*Assistant Examiner*—Yate K Cutliff
(74) *Attorney, Agent, or Firm*—Dominick G. Vicari

(57) ABSTRACT

This invention discloses a process to improve reaction stability in the Direct Synthesis of trialkoxysilanes. The process is particularly effective in the Direct Synthesis of triethoxysilane and its higher alkyl cognates providing improved triethoxysilane yields.

38 Claims, 1 Drawing Sheet

U.S. PATENT DOCUMENTS

| | | | |
|---|---|---|---|
| 5,334,738 A | | 8/1994 | Pachaly et al. |
| 5,362,897 A | * | 11/1994 | Harada et al. ............... 556/470 |
| 5,527,937 A | | 6/1996 | Standke et al. |
| 5,714,131 A | | 2/1998 | Margaria et al. |
| 5,728,858 A | | 3/1998 | Lewis et al. |
| 5,759,230 A | | 6/1998 | Chow et al. |
| 5,770,172 A | | 6/1998 | Linehan et al. |
| 5,783,720 A | | 7/1998 | Mendicino et al. |
| 5,973,177 A | | 10/1999 | Kuivila et al. |
| 6,090,965 A | | 7/2000 | Lewis et al. |
| 6,099,965 A | | 8/2000 | Tennent et al. |
| 6,166,237 A | | 12/2000 | Simandan et al. |
| 6,258,970 B1 | | 7/2001 | Ward, III et al. |
| 6,380,414 B2 | | 4/2002 | Brand |
| 6,580,000 B1 | | 6/2003 | Anderson et al. |
| 6,680,399 B2 | | 1/2004 | Anderson et al. |
| 2002/0010354 A1 | | 1/2002 | Brand |
| 2003/0065204 A1 | * | 4/2003 | Lewis et al. ................ 556/472 |
| 2007/0060764 A1 | | 3/2007 | Lewis et al. |

FOREIGN PATENT DOCUMENTS

| | | |
|---|---|---|
| EP | 784 072 | 7/1997 |
| JP | 55 28928 | 2/1980 |
| JP | 55-28929 | 2/1980 |
| JP | 55 76891 | 6/1980 |
| JP | 57 108094 | 7/1982 |
| JP | 62 96433 | 5/1987 |
| JP | 11 293308 | 8/1998 |
| JP | 11 21288 | 1/1999 |
| WO | WO 85/05047 | 11/1985 |
| WO | WO 01/47937 | 7/2001 |
| WO | 02/60909 | 8/2002 |
| WO | WO 02/060909 | 8/2002 |
| WO | WO 03/060623 | 7/2003 |

OTHER PUBLICATIONS

Dianzeng et al. (1998) "Sythesis of Cuo Nanometer Powder by One Step Solid State Reaction at Room Temperature" *Science Press* 7:43 p. 571-574.

Brunauer, Stephen et al. (1938) "Adsorption of Gases in Multimolecular Layers" 60 p. 309-319.

Suzuki et al. (1994) *Bulletin of the Chemical Society of Japan*, 1 p. 3445-3447.

HM Kingston, "Microwaved-Enhanced Chemistry" *American Chemical Society US* XP001061404, p. 523-550.

* cited by examiner

PROCESS FOR THE DIRECT SYNTHESIS OF TRIALKOXYSILANE

This invention relates to the production of trialkoxysilanes by the catalyzed reaction of silicon with alcohols. More particularly, the invention discloses cyanide and nitrile additives to promote increased silicon conversion when ethanol, propanol and other higher alcohols are the reactants. This Direct Synthesis exhibits high selectivity to the trialkoxysilanes, high overall silicon conversion and high, stable reaction rates.

BACKGROUND OF THE INVENTION

Trialkoxysilanes, especially trimethoxysilane, triethoxysilane and tri(isopropoxy)silane, are used in the production of silane coupling agents. One method of synthesis of trialkoxysilanes is directly from silicon and an alcohol in the presence of copper or a copper compound. This method is known variously in the art as the Direct Synthesis, the Direct Reaction, the Direct Process or the Rochow Reaction. For trialkoxysilanes, it is most conveniently performed in slurry reactors. In a slurry reactor for the Direct Synthesis of trialkoxysilanes, catalytically-activated silicon particles are maintained in suspension in a thermally stable, high boiling solvent and are made to react with an alcohol at an elevated temperature. The trialkoxysilane product is recovered by distillation.

The rate of the Direct Synthesis of a trialkoxysilane is the temporal consumption of the raw materials, i.e., alcohol or silicon, or the temporal formation of products, i.e., trialkoxysilane, and optionally including byproducts. Familiar units are weight percent silicon conversion per hour, or kilograms product per kilogram silicon per hour.

Selectivity is the preference for the trialkoxysilane under the reaction conditions. It is expressed herein as the gravimetric ratio, i.e., trialkoxysilane/tetraalkoxysilane. However, some publications use the molar percentage, 100 (moles trialkoxysilane/molar sum of all silicon-containing products).

Stability of the reaction is the maintenance of desirable rate and selectivity until all raw materials are consumed, or consumed beyond a preset criterion. The progress of the Direct Synthesis can be monitored by determining product composition and/or reaction rate as a function of time or silicon conversion. In general, the profile shows an initial period, termed the induction period, of increasing rate and increasing trialkoxysilane concentration in the reaction mixture, after which the reaction settles into a steady state. In this state, the composition of the reaction mixture remains approximately constant. A period of declining rate and decreasing trialkoxysilane content in the product mixture follows the steady state.

Prior art production of trialkoxysilanes with catalyzed reactions of silicon and alcohols is well known. For example, Rochow, U.S. Pat. No. 3,641,077, discloses a slurry-phase preparation of trialkoxysilanes by directly reacting copper-silicon mass, suspended in silicone oil, with alcohol at 250-300° C. The copper-silicon mass contains about 10 weight percent copper and is prepared by heating copper and silicon above 1000° C. in a furnace in a stream of hydrogen gas. Improved selectivity is displayed in U.S. Pat. No. 3,775,457 to Muraoka et al. wherein polyaromatic hydrocarbon oils are used as solvents in the Direct Synthesis of trialkoxysilanes from an alcohol and finely divided silicon metal activated with cuprous chloride catalyst and HF or HCl.

Suzuki, et al. in Japanese Kokai Tokkyo Koho 55-28929 (1980) acknowledge that activation of silicon with CuCl does not always lead to desirable rate and selectivity. The patent teaches treatment of CuCl with nitrites, naphthalenes, biphenyls and anthracenes prior to its use in the Direct Synthesis. The use of acetonitrile—treated CuCl afforded a rate increase early in the reaction, but this improvement was not sustained at longer reaction times. Selectivity declined considerably relative to the control.

U.S. Pat. No. 4,727,173, to Mendicino, teaches the use of copper (II) hydroxide catalyst to avoid the limitations associated with cuprous chloride and provides a high selectivity to trialkoxysilanes.

U.S. Pat. Nos. 6,580,000 and 6,680,399, disclose the use of copper (II) organophosphate salts and tetraalkyl orthosilicates for the Direct Synthesis of triethoxysilane. However, the processes disclosed therein produce reaction mixtures with selectivity less than one and up to about three.

In U.S. Pat. No. 5,728,858, Lewis, et al disclose that when copper (II) hydroxide is used in combination with alkylated benzene solvents, such as dodecylbenzene, the Direct Synthesis of trialkoxysilanes becomes unstable after approximately 25-35 weight percent of the silicon has been reacted. When methanol is the alcohol reactant at temperatures above about 220° C., trimethoxysilane content in the reaction product declines from approximately 90-95 weight percent to approximately 50-60 weight percent and recovers again to between 80-95 weight percent after about 60 percent silicon conversion. Simultaneous with this loss of selectivity is the enhanced formation of methane, water and dimethyl ether. Methane and dimethyl ether formation represent inefficient use of the methanol reagent. Water reacts with trialkoxysilanes and tetraalkoxysilanes to produce soluble, gelled and/or resinous organic silicates. Formation of these silicates represents inefficiency in the Direct Process. Additionally, the silicates contribute to foaming and incomplete recovery of the reaction solvent as disclosed in U.S. Pat. Nos. 5,783,720 and 6,090,965. U.S. Pat. No. 5,728,858 teaches the reductive activation of copper (II) hydroxide/silicon slurries with hydrogen gas, carbon monoxide, monosilane or polyaromatic hydrocarbons to obtain desirably active, selective and stable Direct Synthesis of trialkoxysilanes in alkylated benzene solvents, such as the linear alkylate, NALKYLENE® 550BL. Reductive activation affords a steady-state region between about 10-70 weight percent silicon conversion, increased silicon conversion and increased selectivity to trimethoxysilane.

The reaction profile described above is generally observed in the Direct Reaction with methanol, but not with the higher alcohols. These alcohols show a maximum in trialkoxysilane formation followed by a decline, with no intervening steady-state period. Some patents, for example, U.S. Pat. Nos. 3,775,457; 5,527,937 and Japanese Kokai Patent Application 6-306083 (1994)) have hinted at this difference with remarks about "waning reactivity" or "maxima in triethoxysilane formation" with time. The rate versus time plots published by Okamoto, et al., *J. Catalysis*, 143 (1993) pp 64-85 and 147 (1994) pp 15-2, for the Direct Synthesis of trialkoxysilanes in fixed bed reactors show distinct maxima at short reaction times (low silicon conversion) followed by deactivation at longer reaction times (higher silicon conversion) for all temperatures (200-280° C.) investigated. The authors report silicon conversions of 73-92 percent and selectivity 0.26-78 for the Direct Synthesis of triethoxysilane. They also observed this peaked reaction profile for Direct Synthesis of trialkoxysilanes in an autoclave (See *J. Organometallic Chem.*, 489 (1995) C12-C16).

Alcohol dehydration and dehydrogenation are especially troublesome problems when ethanol and other higher homologs are used in the Direct Synthesis. At some temperatures (>250° C.), alkenes, aldehydes and acetals, and not the desired trialkoxysilanes, are formed in significant amounts.

Even when these are not the predominant products, their presence in the reaction mixture can result in the inhibition of further catalytic activity. At lower temperatures, (for example 180-220° C.) alcohol decomposition reactions are less prevalent, but the Direct Synthesis is slower.

Co-pending published U.S. patent application Ser. No. 09/974,092, incorporated herein by reference, discloses a process for using nanosized copper and nanosized copper compounds as the sources of catalytic copper for the Direct Synthesis of trialkoxysilanes. Nanosized copper yields high dispersion of catalytic sites on silicon and contributes to improved rate, selectivity and stability at the lower temperatures.

However, in spite of the improvements and advances taught in the cited prior art, there continues to exist the need for a stable, highly selective and rapid Direct Synthesis of trialkoxysilanes, which consumes the raw materials, especially ethanol, propanol and higher alcohols, efficiently, produces less wastes and avoids the deficiencies of unsteady state (peaked profile) operation. In particular, there is a need for such a Direct Synthesis, which exhibits a long period of stable reaction rates and selectivity in its reaction profile. There is also a continuing need for a Direct Synthesis which eliminates or avoids the alcohol reduction, alcohol dehydrogenation and alcohol dehydration side reactions typical of ethanol and the higher alcohols. The present invention provides such a process.

SUMMARY OF THE INVENTION

A process for the Direct Synthesis of trialkoxysilane comprising the steps of:
a) forming a reaction mixture comprising a thermally stable solvent, silicon metal and a catalytically effective amount of a nanosized copper catalyst precursor;
b) agitating and heating the reaction mixture to form copper-activated silicon therein; and,
c) adding to the reaction mixture
(i) an alcohol $R^1OH$ wherein $R^1$ is an alkyl group containing from 1 to 6 carbon atoms,
(ii) a catalyst-promoting amount of at least one CN-containing promoter, the alcohol reacting with the copper-activated silicon to provide trialkoxysilane $HSi(OR^1)_3$ wherein $R^1$ is as defined.

The process of the present invention provides increased catalytic stability and prolongation of the reaction at desirable rates and selectivity. Additionally, the instant invention facilitates continuous and semi-batch manufacturing operation. In semi-batch operation, additional silicon is added to the slurry after 50-80 percent of the previous charge has been consumed and reaction is continued with the alcohol.

DETAILED DESCRIPTION OF THE INVENTION

Figure 1:
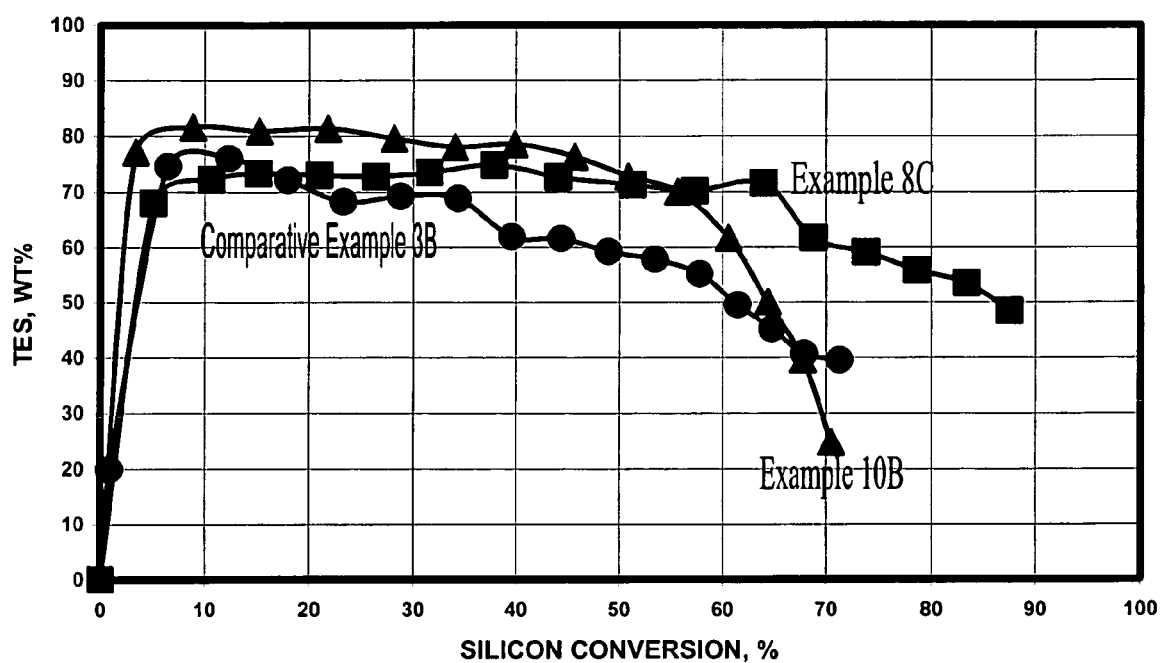
FIG. 1 is a graphical representation of weight percent (wt %) triethoxysilane (TES) versus percent silicon conversion for Comparative Example 3B and Examples 8C and 10B.

The complete process whereby silicon and alcohol are converted into trialkoxysilane and co-products involves physical and chemical phenomena occurring both simultaneously and sequentially. Adequate chemical activity (reaction rate) and selectivity over a certain time period (duration of conversion) are necessary to fulfill specified economic and process engineering requirements. If activity and selectivity decline sharply after attaining desirable values and thereby limit the conversion of raw materials to trialkoxysilanes, then the process is inefficient and unstable. Stability is the maintenance of desirable rate and selectivity until all raw materials are consumed, or consumed beyond a preset criterion. Thus, a steady-state period during which rate and selectivity plateau and are relatively constant contributes to effective process control and efficient raw material utilization.

The following equations are representations of the principal chemical reactions occurring during the Direct Synthesis of trialkoxysilanes with alcohols.

$$Si + 3ROH \rightarrow HSi(OR)_3 + H_2 \quad (1)$$

$$HSi(OR)_3 + ROH \rightarrow Si(OR)_4 + H_2 \quad (2)$$

$$ROH + H_2 \rightarrow RH + H_2O \quad (3)$$

$$2ROH \rightarrow ROR + H_2O \quad (4)$$

$$RCH_2OH \rightarrow R'CH=CH_2 + H_2O \quad (5)$$

$$2Si(OR)_4 + H_2O \rightarrow (RO)_3SiOSi(OR)_3 + 2ROH \quad (6)$$

$$2HSi(OR)_3 + H_2O \rightarrow (RO)_2SiOSi(OR)_2H + 2ROH \quad (7)$$

$$2HSi(OR)_3 + Si(OR)_4 + H_2O \rightarrow HSi(RO)_2SiOSi(OR)_2OSi(OR)_2H + 2ROH \quad (8)$$

$$RCH_2OH \rightarrow RCHO + H_2 \quad (9)$$

$$RCHO + 2RCH_2OH \rightarrow RCH(OCH_2R)_2 + H_2O \quad (10)$$

$$RR''CHOH \rightarrow RR''CO + H_2 \quad (11)$$

The desirable products of the instant Direct Synthesis are trialkoxysilanes of general formula, $HSi(OR)_3$, wherein R is an alkyl group of 1 to 6 carbon atoms. R is preferably methyl, ethyl, propyl and isopropyl. Byproducts of the synthesis are $Si(OR)_4$, $RSiH(OR)_2$, $RSi(OR)_3$, linear, branched and cyclic silicates such as $(RO)_3SiOSi(OR)_3$, $H(RO)_2SiOSi(OR)_2H$, $HSi(RO)_2SiOSi(OR)_3$, $(RO)_3SiOSi(OR)_2R$, $(RO)_3SiOSi(RO)_2OSi(RO)_3$, $(RO)_3SiOSi(OR)HOSi(OR)_3$, $(RO)_3SiOSi(OR)ROSi(OR)_3$, $(RO)Si[OSi(OR)_3]_3$, $(RO)_3SiOSi(OR)(OSi(RO)_3)OSi(OR)_3$, and $[OSi(OR)_2]_n$, (n=4, 5 . . . ), hydrogen gas, hydrocarbons (RH) such as methane and ethane, alkenes (R'CH=CH$_2$) such as ethylene, ethers (ROR) such as dimethyl ether and diethyl ether, aldehydes (RCHO) such as acetaldehyde, acetals (RCH(OCH$_2$R)$_2$) such as 1,1-diethoxyethane and ketones (RR''CO) such as acetone. In the general formula, R'CH=CH$_2$, for the alkene byproducts, R' is hydrogen or an alkyl group of 1 to 4 carbon atoms. In the general formula, RR''CO, for the ketone byproducts of a secondary alcohol (RR''CHOH), R'' and R are both alkyl groups, which can be the same or different. Hydrogen gas, hydrocarbons, volatile aldehydes, ketones and the ethers are typically not condensed in the cold trap with the liquid products and exit the apparatus as a gaseous stream. Some of the silicates are volatilized out of the reactor and are soluble in the liquid reaction product. Others remain solublized in the solvent or precipitate as insoluble gels. The acetals (RCH(OCH$_2$R)$_2$) and less volatile aldehydes and ketones are condensed in the liquid reaction mixture.

The gaseous product stream contains hydrogen gas, hydrocarbons, ethers, volatile aldehydes and ketones and inerting agents such as nitrogen or argon. Analytical methods based on gas chromatography, Fourier Transform Infra-red spectroscopy (FTIR) or mass spectrometry may be used to identify and quantify these components in the gaseous effluent. Assuming that the reaction of Equation 1 produces most of the hydrogen gas in the effluent, the hydrogen generated in the Direct Synthesis can be used as an approximate measure of reaction rate and silicon conversion. Hydrocarbon and ether formation depicted in Equations 3-5, and aldehyde, acetal and ketone formation in Equations 9-1, can be used as measures of the inefficiency of alcohol conversion. It is desirable that less than 2 weight percent of the alcohol fed to the reaction be converted to hydrocarbons, ethers, aldehydes, acetals and ketones and most desirable than none be so converted.

Gas chromatographic (GC) analysis has been found to be a reliable and accurate technique to quantify the composition of the liquid reaction product. Other methods such as nuclear magnetic resonance (NMR) and mass spectrometry (MS) may also be used. These are particularly useful for identifying and quantifying the higher molecular weight silicates contained in the reaction product and reaction solvent. Data on the composition and weight of the reaction product and the fraction of silicon in each of the components are used to calculate the silicon conversion.

Gravimetry and atomic absorption spectroscopy are suitable methods for quantifying the silicon content of the reaction solvent. Analytical procedures are published, for example, in The Analytical Chemistry of Silicones, Chapter 8, (A. L. Smith, Editor), John Wiley & Sons Inc., NY, 1991. Soluble silicates retained in the reaction solvent are a measure of the extent to which side reactions such as those in Equations 6-8 have occurred. All of these reactions depend on the presence of water, which is formed, for example, by the reaction of Equations 3-5 and 10. Gels and soluble silicates contained in the reaction solvent can be removed according to the methods disclosed by Bailey, et al. in U.S. Pat. No. 5,166,384, or by Lewis, et al. in U.S. Pat. No. 6,090,965 or by Simandan, et al. in U.S. Pat. No. 6,166,237, all of which are hereby incorporated herein by reference.

U.S. Pat. No. 4,727,173 to Mendicino and U.S. Pat. No. 5,728,858 to Lewis, et al. disclose processes for the Direct Synthesis of trimethoxysilane wherein product selectivity>20, rates 5-10 percent silicon conversion per hour and overall silicon conversion>85 percent are reproducibly attainable at 250-280° C. In batchwise reactions, a steady-state region exists from about 10 weight percent silicon conversion to about 70 weight percent silicon conversion during which the content of trimethoxysilane in the reaction mixture is approximately constant and generally >85 weight percent and the selectivity>20. However, the cognate synthesis of triethoxysilane, tri(propoxy)silane and other higher homologs does not proceed straightforwardly under the same reaction conditions. Trialkoxysilane formation rises sharply early in the reaction and falls thereafter. There is no discernable steady-state and reaction stability (i.e., the extent of silicon conversion) is poor, typically 10-30 percent silicon conversion to products before reaction stops. Considerable aldehyde, ketone and acetal byproduct formation also accompanies this poor reaction stability. Accordingly, in one embodiment of the invention, lower reaction temperatures and cyano or nitrile additives are required to minimize or obviate the interfering and deactivating side reactions and sustain the Direct Synthesis to high silicon conversions.

In one embodiment of the present invention, trialkoxysilanes comprises at least about 80 weight percent of the liquid reaction products, and according to another embodiment at least about 85 weight percent, of the liquid reaction products.

According to one embodiment of the invention, levels of the alkyl silicates, $Si(OR)_4$, are less than about 9 weight percent, and in another embodiment are less than about 6 weight percent. In yet another embodiment of the invention, $(RO)_2SiH_2$, $RSiH(OR)_2$ and $RSi(OR)_3$ compounds are individually less than about 2 weight percent and less than 1 weight percent in still another embodiment. Condensed silicates are maximally about 1 weight percent and preferably less than 0.5 weight percent. In addition to the percentage ranges taught hereinabove, selectivity to the desired trialkoxysilanes may also be expressed as the gravimetric ratio, i.e., $HSi(OR)_3/Si(OR)_4$.

In one embodiment of the invention, the gravimetric ratio is at least about 9 when computed over the total course of a reaction. This overall value is also referred to herein as the product selectivity to distinguish it from the selectivity of individual samples taken during the course of a reaction. According to one other embodiment of the invention, the gravimetric ratio (i.e., product selectivity) is at least about 15 and in another embodiment is at least about 30, especially at the outset and during the steady-state portion of the reaction.

Reaction rate is typically expressed as silicon conversion per unit time, but it might also be expressed as alcohol conversion per unit time, or as space time yield (product output per unit weight of raw material per unit time). It is desirable to have reaction rates, which provide a good balance between product formation and heat removal (temperature control) from the reactor. In one embodiment of the present invention, the reaction rate is more than about 4 weight percent silicon conversion per hour, and in another embodiment is from about 5 to about 20 percent silicon conversion per hour. It is also desirable that the induction time, that is the interval between the onset of reaction and the attainment of both steady-state rate and product composition, be very short, preferably less than 4 hours and most preferably less than 1 hour. According to one embodiment of the invention, the maximum amount of silicon consumed during the induction time is about 15 weight percent, and in another embodiment is less than about 10 weight percent.

Rate and trialkoxysilane content of the reaction product can rise to maximum values and remain relatively constant up to and beyond about forty percent silicon conversion, or they can decline linearly or exponentially to lower values, even to zero. In the latter case, silicon conversions in excess of fifty percent might be achieved before reaction stops completely, but the process will be inefficient in raw material consumption and will possibly exhibit low selectivity. Steady-state is characterized by the existence of a plateau region in the reaction profile. In the Direct Synthesis of triethoxysilane and the higher trialkoxysilanes, it is desirable that steady-state extends beyond about fifty percent silicon conversion, and particularly desirable that it extends beyond seventy percent, even to ninety percent silicon conversion. When both rate and selectivity decline from steady-state values as time (and silicon conversion) increases, it is preferable that the decline be slow and linear rather than be rapid or exponential.

The decline of rate and selectivity can be due to one or more deactivation phenomena such as poisoning of active sites, fouling of the reactive surface by deposition or blockage, loss of surface area by sintering and destruction of active sites or reactive intermediates. It is customary in the art to calculate the rate or selectivity during the deactivation stage relative to the maximum rate or selectivity and to plot this ratio versus time or conversion to determine the severity of the deactivation (see Catalyst Deactivation 1991, C. H. Bartholomew and J. B. Butt, Editors, Elsevier, Amsterdam, 1991. G. F. Froment, pp 53-83). Since the slopes of the plots are negative, the more negative the slope the more severe is the deactivation. Thus, acceptable reaction stability requires that the ratios be about 1 and the slopes of the plots approach zero. It will be shown by example that slopes and ratios approach these criteria for the Direct Synthesis of trimethoxysilane in the absence of promoters, but that marked deviations are characteristic of triethoxysilane under the same or similar conditions.

Another criterion for improved reaction stability is avoidance or delay of deactivation. The later the onset of deactivation the more stable is the reaction. It has been observed that delayed deactivation can sometimes be quite rapid. However, more desirable conversion of raw material to products will have occurred before the deactivation.

Reaction stability is the maintenance of desirable rate and selectivity until all of the silicon is consumed or is consumed to a predetermined criterion. Thus, the extent of silicon conversion is a quantitative measure of reaction stability. According to one embodiment of the invention, the silicon conversions is greater than about 70 weight percent, and in another embodiment is greater than 85 weight percent and in yet another embodiment is greater than 90 weight percent. The instant invention also teaches the use of cyanides and nitrites to obtain reaction profiles (plot of concentration of trialkoxysilane in product mixture versus reaction time or silicon conversion) that show no, or considerably less, catalytic deactivation compared to the appropriate controls.

Organic and Inorganic Cyanide Promoters

The term "promoter" as used herein is defined as an additive that extends silicon conversion at desirable reaction rates and selectivity to the trialkoxysilane. Promoters cause the sharp maxima in trialkoxysilane formation to be replaced by a flatter reaction profile. Simultaneously, the promoters ameliorate the deactivation so that the decreases in rate and selectivity between about 10 to about 70 percent silicon conversion are considerably slower, or are delayed, compared to when they are not used. Thus, the promoters contribute to the maintenance of desirable rate and selectivity and so improve reaction stability.

According to one embodiment of the present invention, suitable promoters are those compounds possessing CN functionality, e.g., organonitriles and inorganic cyanides that are effective for the Direct Synthesis process of this invention. The promoters include organonitriles with normal boiling points higher than the temperature at which the Direct Synthesis is conducted. Lower boiling nitrites can also be used, but they must be continuously or periodically supplied to the reaction mixture and provision must be made for their separation from the trialkoxysilane product. According to one aspect of the invention, the promoter possesses the general formula $X-(CN)_n$ wherein X is hydrogen, a metal or an organic group $R^2$, and n is 1 to 4 with the valence of X being equal to n. In another embodiment of the invention, $R^2$ is a hydrocarbon group containing up to about 40 carbon atoms, optionally, containing silicon and/or etheric oxygen. In still another embodiment of the invention, $R^2$ is an aliphatic, cycloalpihatic, aryl, or alkaryl group containing four or more carbon atoms. In yet another embodiment of the invention, suitable nitrites are those of the general formula $CH_3(CH_2)_nCN$, wherein n is an integer of about 4 to about 9, such as, for example, acetonitrile, t-butyl nitrile, cyclohexyl nitrile, benzonitrile, benzyl nitrile and the like. In another embodiment of the invention, $R^2$ can also contain functional groups, which will not interfere with the conduct of the desired trialkoxysilane Direct Synthesis. Thus, $R^2$ can contain ether (—C—O—C—) groups. According to one aspect of the invention, suitable examples of $R^2$ include cyanoalkyl ethers of general formula, $RO(CH_2)_nCN$ and $[CN(CH_2CH_2)_y]_2O$, wherein n is an integer from about 1 to about 12 and y is an integer from 1 to 20, and in another aspect of the invention n is an integer from about 4 to about 10 and y is an integer from about 1 to about 4.

According to an embodiment of the invention, n of the general formula $X-(CN)_n$ is 1, and $R^2$ is an etheric oxygen-containing group $R^3OR^4$ in which $R^3$ is a monovalent hydrocarbon group and $R^4$ is a divalent hydrocarbon group, there being up to about 40 carbon atoms total in the etheric oxygen-containing group.

According to another embodiment of the invention, n of the general formula $X-(CN)_n$ is 1 and $R^2$ is an etheric oxygen-containing group $R^5OR^6$ in which $R^5$ and $R^6$ are divalent hydrocarbon groups, there being up to about 40 carbon atoms total in the etheric oxygen-containing group.

Lower boiling nitrites like acetonitrile (normal boiling point 82° C.) have been previously disclosed as agents to activate CuCl for reaction with silicon. However, the nitrile was removed before the solid CuCl was mixed with silicon for the accomplishment of the Direct Synthesis. It will be shown by example, as more fully described below, that a solution of "dry process" CuCl in acetonitrile activates silicon effectively and promotes increased silicon conversion.

In another embodiment, other suitable monofunctional nitrites useful as promoters of the Direct Synthesis of the instant invention include compounds of general formula, $CN(CH_2)_nSi(Y)_3$, wherein x is an integer greater than or equal to zero, and is preferably from about 2 to about 8, and Y is an aliphatic, cycloalpihatic, aryl, or alkaryl group, or an alkoxy group, OR', in which R' is alkyl or aryl, methyl, ethyl and propyl. In one embodiment of the invention, the radical, R', is the same as that of the alcohol used in the Direct Synthesis. In another embodiment of the invention, R' is $CN(CH_2)_xSi(OR')_3$ in which x is 3 or 4 and R' is $CH_3$, $C_2H_5$ or $C_3H_7$.

In another embodiment of the invention, n of the general formula $X-(CN)_n$ is 1 and R2 is

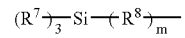

$$(R^7)_{\overline{3}}Si-(R^8)_{\overline{m}}$$

in which each $R^7$ is the same or different monovalent hydrocarbon group of up to about 12 carbon atoms, one or more of which optionally contain etheric oxygen, $R^8$ is a divalent hydrocarbon group of up to about 10 carbon atoms and m is 0 or 1.

In still another embodiment of the invention, other effective promoters include difunctional, trifunctional and other multifunctional nitriles for stability during the Direct Synthesis of trialkoxysilanes. Difunctional organonitriles have two cyano groups per molecule. These may be on the same carbon atom, as for example in malonitrile, $CH_2(CN)_2$, and 1,1-dicyanocyclohexane, or on different carbon atoms as in 1,2-dicyanobenzene, α,ω-dicyanoalkanes and 1,4-dicyanocyclohexane. In one particular embodiment of the invention, the promoters are α,ω-dicyanoalkanes. They have general formula, $CN(CH_2)_xCN$, in which x is an integer greater than or equal to one, and according to one embodiment of the invention, x is an integer from about 4 to about 9.

According to one embodiment of the invention, other difunctional nitrile promoters include compounds of general formula, $[CN(CH_2)_x]_2Si(Y)_2$. In the general formula, Y has the same meaning as hereinabove defined and x is an integer greater than or equal to zero, and preferably is from about 2 to about 8. In another embodiment of the invention, the promoters include those of the general formula $[CN(CH_2)_x]_2Si(OR')_2$ wherein x is about 3 or about 4 and R' is $CH_3$, $C_2H_5$ or $C_3H_7$.

In another embodiment of the invention, n of the general formula $X-(CN)_n$ is 2 and $R^2$ is

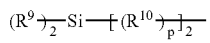

in which each $R^9$ is the same or different monovalent hydrocarbon group of up to about 12 carbon atoms, one or both of which optionally contain etheric oxygen, each $R^{10}$ is the same or different divalent hydrocarbon group of up to about 10 carbon atoms and p is 0 or 1.

The trifunctional organonitriles have three cyano groups per molecule. These can be on the same carbon atom as in $R''C(CN)_3$, in which R'' is hydrogen, an aliphatic, cycloalpihatic, aryl, or alkaryl group, or on different carbon atoms as in 2,4,6-tricyanotoluene, 1, 3, 5-tricyanobenzene and the variously substituted isomeric tricyanoalkanes. In another embodiment, the trifunctional organonitrile is a tricyanoalkoxyalkane such as tricyanoethoxypropane. According to one embodiment of the invention, trifunctional nitrile promoters include compounds of general formula, $[CN(CH_2)_x]_3SiY$, in which Y has the same meaning as hereinabove defined and x is an integer greater than or equal to zero, and preferably is from about 2 to about 8. In another embodiment the promoters include trifunctional nitrile promoters of general formula, $[CN(CH_2)_x]_3SiY$ wherein x is an integer from about 3 or about 4 and R' is $CH_3$, $C_2H_5$ or $C_3H_7$.

According to another embodiment of the invention, n of the general formula $X-(CN)_n$ is 3 and $R^2$ is

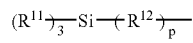

in which each $R^{11}$ is the same or different monovalent hydrocarbon group of up to about 12 carbon atoms, one or both of which optionally contain etheric oxygen, each $R^{12}$ is the same or different divalent hydrocarbon group of up to about 10 carbon atoms and p is 1.

In the context of this invention, compounds with four or more cyano groups per molecule are termed multifunctional. They comprise aliphatic compounds like 1,1,2,2-tetracyanoethane, aromatic compounds like 1,2,4,5-tetracyanobenzene, and cycloaliphatic compounds like 2,2,3,3-tetracyanoethylene oxide.

Accordingly, inorganic cyanides like HCN, LiCN, NaCN, KCN, CuCN, AgCN, $Mg(CN)_2$, $Ni(CN)_2$, $Pd(CN)_2$ and $Si(CN)_4$ are effective promoters of reaction stability in the Direct Synthesis of trialkoxysilanes. In one particular embodiment, CuCN is the promoter of the Direct Synthesis of trialkoxysilanes. It can be added alone or in combination with the copper catalyst precursors (vide infra). In another embodiment of the invention, the CuCN promoter is made by treating nanosized $Cu_2O$ or nanosized CuCl and their mixtures with gaseous HCN.

Solid promoters like the inorganic cyanides can have particle sizes that range from between about 10 micrometers and about 0.1 nanometer. According to one aspect of the invention, the particle size is less than about 1 micrometer and in another aspect of the invention is the particle size be between about 1 and about 600 nanometers. Particle sizes in this latter range are described as nanosized.

Liquid and solid promoters can be added to the reactor at the outset of the reaction, or intermittently or continuously during the process. In one embodiment of of the invention the liquid and/or solid promoters are added at the outset of the reaction. When intermittent or continuous addition is selected, the promoter can be introduced separately or admixed with the alcohol stream, the solvent, or silicon and copper sources, depending on considerations such as cost, convenience and safety. In another embodiment of the invention, mixtures of promoters are effectively employed to promote reaction stability. In another embodiment of the invention, the Direct Synthesis of triethoxysilane is prepared with a mixture of CuCN and organonitriles to provide extended reaction stability to beyond about fifty percent silicon conversion.

The promoters used in the Direct Process of this invention are present in an amount effective to extend silicon conversion at desirable reaction rates and selectivity. Generally, an effective amount is determined by factors such as the physical form, the particle size, the boiling point and the number of cyano groups per molecule. Thus, liquids are generally more potent than solids, nanosized solids are more effective than those of conventional particle size, organo nitrites with normal boiling points greater than the reaction temperature are more effective than those with lower boiling points, and dicyano compounds are more effective than the monofunctional ones.

In one embodiment of the invention, the solid inorganic cyano compounds, e.g., CuCN, are present in a range of about 100 parts per million to about 10 weight percent based on the weight of silicon charged to the reactor, or actually present in the reactor. According to another embodiment of the invention, the range for solid inorganic cyano compounds is about 1000 parts per million to about 4 weight percent. In another embodiment of the invention, the liquid organo nitrites, are present in a range of about 100 parts per million to 6 weight percent, and in another embodiment they are present in a range of about 200 parts per million to about 4 weight percent on the same basis.

Copper Catalyst Precursors

The copper and copper compounds useful as starting materials to activate silicon for Direct Reactions with alcohols are not themselves the actual catalysts for the instant Direct Synthesis invention. When the slurry comprising copper and/or a copper compound, silicon and a thermally stable, reaction solvent is heated, the copper and silicon interact to produce the actual catalytic phase that reacts with the alcohol. It is generally accepted that the actual catalysts are copper-silicon alloys, intermetallics and/or solid solutions formed by the diffusion of copper into silicon, or by the reaction of copper compounds with silicon. Thus, the copper-containing raw materials are copper catalyst precursors and will be so described herein.

Copper, copper (I) oxide, copper (II) oxide, copper (I) chloride, copper (II) chloride, copper (II) hydroxide, mixed hydrous oxides (for example, $3CuO.Cu(OH)_2$), basic copper carbonate ($CuCO_3.Cu(OH)_2$), copper carboxylates, copper alkoxides and mixtures thereof are copper sources, which can be used to activate silicon for the Direct Synthesis of trialkoxysilanes. These solids are typically 1-10 micrometers in particle size. They can be used effectively in the practice of the instant invention.

Nanometer sized particles have diameters in the range from about 1 nanometer ($10^{-9}$ meter) to about 100 nanometers ($10^{-7}$ meter). These materials are also described in the art as nanostructured, nanocrystalline, nanosized, nanoscale, ultrafine or superfine. Their structures and high surface to volume ratio make them desirable in catalytic, electronic, magnetic and coating (pigment) applications. When compared with the conventional copper catalysts for the Direct Synthesis of trialkoxysilanes, nanometer sized particles are 10 to 100 fold smaller in diameter. Nanosized copper sources are preferred in the practice of the instant invention. The preparation of nanosized copper, copper (I) chloride, copper (I) oxide, copper (II) oxide and other catalyst precursors relevant to the instant invention is disclosed in the co-pending applications entitled, Preparation of Nanosized Copper and Nanosized Copper Compounds, WO 02/060623, and Preparation of nanosized copper (I) compounds, published U.S. patent application Ser. No. 10/413,754, the entire contents of which are incorporated herein by reference. Various other physical and chemical methods are known in the art for the preparation of nanosized copper and copper compounds.

Copper catalyst precursors for use in the present invention are preferably anhydrous, but material containing adventitious water or water of hydration is also usable. If a hydrated, copper catalyst precursor is used, provision must be made in the design of the apparatus to avoid contact of the water formed during its dehydration and thermal decomposition with the trialkoxysilane reaction product. Additionally, alcohol introduction into the reaction slurry must be delayed until the dehydration and thermal decomposition are complete. This is usually at temperatures greater than 150-180° C. at ambient pressure.

Copper catalysts precursors with particle sizes from about 1 to about 10 micrometers are effective in the process of the instant invention. However, nanosized precursors are even more effective. The nanosized precursors have particle sizes from about 0.1 to about 600 nanometers, preferably from about 0.1 to about 500 nanometers and most preferably from about 0.1 to about 100 nanometers.

In addition to particle size and water content, various other criteria can be used to characterize the nanosized copper catalyst precursors of this invention. BET surface area of the precursors can be as low as 0.1 m$^2$/g. Areas greater than 10 m$^2$/g are preferred and greater than 15 m$^2$/g are particularly preferred.

Trace impurities and extraneous matter might be present in the nanosized copper catalyst precursors depending on the method and conditions of its preparation. Thus, trace amounts of aluminum, barium, calcium, chromium, iron, lead, magnesium, manganese, nickel, phosphorus, sodium, tin and zinc might be present in the commercial CuCl, Cu(OH)$_2$, CUCO$_3$.Cu(OH)$_2$, and 3CuO.Cu(OH)$_2$ and in nanosized copper and copper oxides produced by the processes of the co-pending applications on nanosized copper and copper oxides (loc. cit.), as well as by those of U.S. Pat. Nos. 4,539,041 and 5,759,230, incorporated herein by reference. Tolerable and limiting quantities of the pertinent metals are defined herein below. Polymers, surfactants and boron contamination might be present in nanoparticulate copper generated by borohydride reduction in the presence of stabilizing polymers, or in reverse micelles and microemulsions.

Zinc content of the copper catalyst precursor is desirably less than 2500 parts per million, preferably less than 1500 parts per million and most preferably less than 750 parts per million. Based on the initial weight of silicon charged to the reactor, zinc content of the reaction slurry must be less than 100 parts per million, and preferably less than 50 parts per million. The other critical trace element, which can be contained in the catalyst precursor, is lead (Pb). Its concentration in the slurry must be less than 50 parts per million.

The copper catalyst precursors used in the Direct Process of this invention are present in an amount effective to catalyze the reaction. Generally an effective amount ranges from about 0.01 to about 5 parts by weight of catalyst precursor per 100 parts by weight of the silicon metal. The smaller particle size and higher surface area of the nanosized copper catalyst precursors preferred in the instant invention afford higher dispersion of the actual catalytic phases on the silicon surface. Accordingly, usage of nanosized copper catalyst precursors in amounts in the lower part of the broad range is unusually effective in initiating and sustaining selective synthesis of trialkoxysilanes. Thus, about 0.05 to about 2 parts by weight of the nanosized copper catalyst precursor per 100 parts by weight silicon is preferred and about 0.08 to about 1 part by weight per 100 parts by weight silicon is especially preferred. Expressed in terms of parts by weight copper per 100 parts by weight silicon, the effective range is 0.008-4.5 parts copper, the preferred range is 0.03-1.8 parts copper and the specially preferred range is 0.05-0.9 parts.

Silicon

The silicon metal reactant used in the process of this invention can be any commercially available grade of silicon in particulate form. It may be produced by any of the methods in current practice such as casting, water granulation, atomization and acid leaching. These methods are more fully described in Silicon for the Chemical Industry, (H. Oye, et al, Editors), vol. I (pp 39-52), vol. II (pp 55-80), vol. III (pp 33-56, 87-94), Tapir Publishers, Norwegian Institute of Technology, and in U.S. Pat. Nos. 5,258,053; 5,015,751; 5,094,832; 5,128,116; 4,539,194; 3,809,548; 4,539,194, and German Patents Nos. 3,403,091 and 3,343,406. Special types of chemical grade silicon containing controlled concentrations of alloying elements are also suitable, provided that copper is not one of the alloying elements and that the alloying elements are not deleterious to the rate, selectivity and stability of trialkoxysilane Direct Synthesis. Special silicon of this type is described in U.S. Pat. Nos. 5,059,343; 5,714,131; 5,334,738; 5,973,177 and European Patent Nos. 0,494,837 and 0,893,448. A typical composition of commercial silicon metal useful in this invention, expressed in percent by weight, is Si~98.5%, Fe<1%, Al~0.05 to 0.7%, Ca~0.001 to 0.1%; Pb<0.001%, Water<0.1%. Generally, smaller particle sizes are preferred for ease of dispersion in the slurry, faster reaction and minimization of erosion in the reactor. In one embodiment, the particle size is smaller than about 500 micrometers so that reactor erosion is minimized. Sieving of ground silicon to regulate particle size is optional. In another embodiment of the invention, at least about 90 weight percent of the particle size distribution is between about 1 to about 300 micrometers. In yet another embodiment of the invention, at least about 90 weight percent the particle size distribution is between about 1 to about 100 micrometers.

Alcohol

According to one embodiment of the invention, the alcohols which are useful in the process of this invention have the formula R$^1$OH wherein R$^1$ is an alkyl group containing from 1 to 6 carbon atoms, inclusive. In another embodiment, R$^1$ is an alkyl group containing from 1 to 3 carbon atoms inclusive. In yet another embodiment, the alcohols are methanol and ethanol. While it is customary to use a single alcohol in the Direct Process, in one embodiment of the invention, mixtures of two or more can be used to prepare trialkoxysilanes with different alkoxy groups, or to facilitate the reaction of a less reactive alcohol. In one embodiment, about 5 weight percent methanol can be added to ethanol to improve the rate and stability of the Direct Synthesis of triethoxysilane. In yet another embodiment of the invention, the reaction may be initiated with one alcohol and continued with another, or with a mixture of alcohols. Thus, in an embodiment of the invention, copper-activated silicon prepared with nanosized copper catalyst precursors can be reacted initially with methanol and later with ethanol. It is preferable that the alcohol be anhydrous. However, water contents of up to 0.1 weight percent can be tolerated without significant loss of selectivity, reactivity and stability.

Generally, the reaction is run batchwise in a slurry and the alcohol is fed into the slurry as a gas or liquid. Gaseous introduction is preferred. An induction period lasting from a few minutes up to about five hours may be observed. The initial alcohol feed rate is optionally controlled at a low level and increased following the induction period. Similarly, the alcohol feed rate is optionally reduced after about 70 weight percent silicon conversion to minimize the formation of tetraalkoxysilanes. Generally, once the reaction is running, the alcohol feed rate can be adjusted to give the desired level of alcohol conversion. One skilled in the art can readily adjust the feed rate in a given reaction run by monitoring the product composition. If the feed rate is too high the product stream will contain a larger proportion of unreacted alcohol and/or alkyl silicate $Si(OR)_4$.

Reaction Solvent

Solvents for the slurry-phase Direct Synthesis of trialkoxysilanes maintain the copper-activated silicon in a well-dispersed state and facilitate both mass transfer of the alcohol to catalytic sites and heat transfer between the reacting solids and the reactor. The solvents useful in the process of this invention are thermally stable compounds or mixtures that do not degrade under the activation and reaction conditions. Structurally, they are linear and branched paraffins, naphthenes, alkylated benzenes, aromatic ethers, and polyaromatic hydrocarbons. In the latter, the aromatic rings may be fused together as in naphthalene, phenanthrene anthracene and fluorene derivatives. They may be joined by single carbon-carbon bonds as in biphenyl and terphenyl derivatives, or they may be joined by bridging alkyl groups as in the diphenylethanes and tetraphenylbutanes. Suitable solvents include high temperature stable organic solvents typically used as heat exchange media. For example, THERMINOL® 59, THERMINOL® 60, THERMINOL® 66, DOWTHERM® HT, MARLOTHERM® S, MARLOTHERM® L, diphenyl ether, diphenyl and terphenyl and their alkylated derivatives with normal boiling points higher than about 250° C.

THERMINOL® is the Solutia Company trade name for heat transfer fluids. THERMINOL® 59 is a mixture of alkyl-substituted aromatic compounds recommended for use between −45 to 315° C. THERMINOL® 60 is a mixture of polyaromatic compounds with an average molecular weight of 250. Its optimum temperature range is from −45° to 315° C. THERMINOL® 66 and DOWTHERM® HT are mixtures of hydrogenated terphenyls with an average molecular weight of 240. Maximum temperature limit is about 370° C. THERMINOL® 59, THERMINOL® 66 and DOWTHERM® HT are preferred solvents of this invention. DOWTHERM® fluids are produced by Dow Chemical Company.

MARLOTHERM® is the Hüls AG trade name for its heat transfer fluids. MARLOTHERM® S is a mixture of isomeric dibenzylbenzenes. MARLOTHERM® L is a mixture of isomeric benzyl toluenes. Both can be used at temperatures up to about 350° C. Both are preferred solvents for the instant invention.

Suitable alkylated benzenes for the practice of the instant Direct Process are dodecylbenzene, tridecylbenzene, tetradecylbenzene and their mixtures such as are sold by Vista Chemical Company under the trade name NALKYLENE®, and by Condea Augusta s.p.a. under the trade names ISORCHEM® and SIRENE®. NALKYLENE® 550BL, NALKYLENE® 550L, NALKYLENE® 500, NALKYLENE® 501, NALKYLENE® 600L and NALKYLENE® V-7050 are particularly preferred reaction solvents for use with the nanosized CuCl precursors. With nanosized copper and nanosized copper oxides, the alkylated benzene solvents afford better reaction stability and selectivity to the trialkoxysilanes when used at temperatures between 180-220° C.

Naphthenes are cycloparaffins. They are components of white mineral oils, petroleum distillates and some fuels. White mineral oils and petroleum distillates also contain normal and branched paraffins (see A. Debska-Chwaja, et al., Soap, Cosmetics and Chemical Specialties, (November 1994), pp 48-52; ibid., (March 1995) pp64-70). Suitable examples of commercial products containing naphthenes and paraffins and useful as reaction solvents for this invention are the white mineral oils, CARNATION 70, KAYDOL, LP-100 and LP-350, and the petroleum distillates, PD-23, PD-25 and PD-28, all of which are sold by Chemtura Corporation under the WITCO trade name. Other examples of naphthenes useful as reaction solvents are butylcyclohexane, decahydro-naphthalene, perhydroanthracene, perhydrophenanthrene, perhydrofluorene and their alkylated derivatives, bicyclohexyl, perhydroterphenyl, perhydrobinaphthyl and their alkylated derivatives.

Mixtures of alkylated benzenes, naphthenes and normal and branched paraffins with polyaromatic hydrocarbons are also useful as reaction solvents for the instant invention.

Used solvents can be treated with boric acid and borates as described in U.S. Pat. No. 5,166,384, or formic acid as disclosed in U.S. Pat. No. 6,090,965, or by thermal hydrolysis as disclosed in U.S. Pat. No. 6,166,237 and reused in subsequent trialkoxysilane Direct Synthesis reactions. The relevant portions of all of these disclosures are incorporated herein by reference.

Silicon metal, copper catalyst precursor, promoter and solvent can be added together in the reactor in any order. The solvent is present in an amount sufficient to disperse the solid and gaseous reactants homogeneously. According to one embodiment, the reactions are initiated with solvent and solids in a gravimetric ratio between about 1:2 and about 4:1, and in another embodiment between about 1:1 to about 2:1. However, as the silicon is consumed during batchwise Direct Synthesis, the solvent to solids ratio will increase. The ratio can be maintained within narrow limits of the preferred range for continuous reactions.

Copper-Silicon Activation Conditions

Activation is the process of incorporating catalyst, and if desired, other auxiliary agents, into the silicon to make it reactive with the alcohol. Activation may be performed in the same reactor used for the Direct Reaction of the alcohol, or in a separate reactor. In the latter case, the activated silicon is typically and desirably transported to the synthesis reactor in an anhydrous, non-oxidizing atmosphere. Transportation of the activated silicon as a slurry in the reaction solvent is especially preferred.

Activation of copper catalyst precursors and silicon in a slurry reactor is performed at 20-400° C., preferably between 150-300° C., with mixtures containing 0.01-50 weight percent copper relative to silicon. In one embodiment of the invention, the promoter is optionally present during the activation. In another embodiment, the agitated slurry is heated to 200-300° C. in an inert gas (for example, nitrogen or argon) atmosphere for 0.01-24 hours prior to the injection of the alcohol reactant. Time and temperature must be sufficient to bring about effective copper-silicon activation and avoid significant loss of trialkoxysilane selectivity, and/or formation of hydrocarbons and water during the Direct Synthesis. It is not necessary that all of the silicon be present during the activation step. For example, a portion of the silicon to be used and all of the copper catalyst precursor may be activated in the reaction solvent and the remaining silicon added thereafter.

Alternatively, alcohol, optionally admixed with inert gas, is introduced into the agitated slurry of copper catalyst precursor, promoter, silicon and reaction solvent during heating. Reaction ensues beyond some minimum temperature, typically >180° C. at atmospheric pressure. Preferably, alcohol vapor is introduced into an agitated slurry after the temperature is greater than or equal to 180° C.

Activation may also be performed with the silicon and nanosized copper catalyst precursors and nanosized promoters in their dried state in rotary, vibrating, fluidized bed or fixed bed reactors. Thereafter, the activated silicon is transported to the slurry reactor for reaction with the alcohol.

Activation of mixtures comprising silicon and copper catalyst precursors can produce water, aldehydes, carbon monoxide, HCl, silicon tetrachloride and other compounds, depending on the specific precursor charged. These compounds are preferably volatilized and absent prior to the start of the Direct Synthesis of the trialkoxysilanes. If they are present in the synthesis reactor or in the product retention vessel, they can contribute to gel formation, poor reaction selectivity and reduced trialkoxysilane recovery. When CuCl, or another halogen-containing copper precursor is used, provision must be made to protect the reactor and ancilliary equipment from corrosion.

Reaction Conditions

Designs, descriptions and operational considerations pertinent to three phase reactors are contained in the following monograph, articles and patents: A. Ramachandran and R. V. Chaudhari, Three Phase Catalytic Reactors, Gordon and Breach Science Publishers, NY, 1983; N. Gartsman, et al., International Chemical Engineering, vol. 17 (1977) pp 697-702; H. Ying, et al., Industrial & Engineering Chemistry, Process Design & Development, vol. 19 (1980) pp 635-638; N. Satterfield, et al., Chemical Engineering Science, vol. 35 (1980) pp 195-202; M. Boxall, et al., Journal of Metals, (August 1984) pp 58-61; W. Roeckel, C. Scaccia and J. Conti, U.S. Pat. No. 4,328,175 (May 4, 1982); and L. M. Litz, U.S. Pat. No. 4,454,077 (Jun. 12, 1984). The relevant portions of all of these disclosures are incorporated herein by reference.

Reactors may be operated in a batchwise or continuous mode. In batchwise operation, a single addition of silicon and copper catalyst is made to the reactor at the outset and alcohol is added continuously, or intermittently, until the silicon is fully reacted, or reacted to a desired degree of conversion. In continuous operation, silicon and copper catalyst are added to the reactor initially and thereafter to maintain the solids content of the slurry within desired limits. The batchwise mode is illustrated in U.S. Pat. No. 4,727,173 and the continuous mode in U.S. Pat. No. 5,084,590. Both of these patents are incorporated herein by reference.

According to one embodiment of the present invention, the Direct Synthesis of trialkoxysilanes is conducted in a continuously agitated slurry reactor containing thermally stable solvent, silicon, nanosized copper catalyst precursor, nanosized or liquid promoter and foam control agents in contact with alcohol vapor. The number and type of impellers are selected to afford effective solids suspension, gas dispersion and mass transfer of alcohol to the copper-activated silicon. The reactor may have a single nozzle or multiple nozzles for the introduction of gaseous alcohol. A means of continuous or intermittent addition of promoter, activated nanosized copper catalyst precursor-silicon mixture, or of silicon, is also provided. Means for continuous removal and recovery of the volatile reaction products and unreacted alcohol are also desirably provided. Separation and purification of the trialkoxysilane products are optimally performed in the manner disclosed in U.S. Pat. No. 4,761,492 or U.S. Pat. No. 4,999,446, both of which are incorporated herein by reference.

When the initial loading of silicon and nanosized copper catalyst precursor is activated according to the method of the instant invention, continuous slurry phase Direct Synthesis of trialkoxysilanes is advantageously continued by adding only silicon, or silicon containing less nanosized copper catalyst precursor and promoter than that initially added. In this way, the copper concentration of the slurry is controlled to minimize the transformation of the alcohol to hydrocarbons and water as presented in Equations 3 and 5, supra. Disadvantages caused by water have been recited hereinabove.

The reaction is generally conducted at temperatures above about 150° C., but below such a temperature as would degrade or decompose the reactants, promoter, solvents or desired products. Preferably, the reaction temperature is maintained in a range from about 200° C. to about 280° C. The reaction of methanol with the copper-activated silicon of the present invention is preferably operated at 220-270° C., and most preferably 230-260° C., whereas the reaction of ethanol is preferably operated at 190-240° C., and most preferably 200-220° C. The pressure at which the reaction is conducted can be varied from subatmospheric to superatmospheric. Atmospheric pressure is generally employed in the reaction of methanol with copper-activated silicon. Pressures in the range 1-5 atmospheres are advantageous to rate and trialkoxysilane selectivity in the Direct Triethoxysilane Synthesis.

Preferably, the contents of the reaction mixture are agitated to maintain a well-mixed slurry of the copper-activated silicon particles, promoter and gaseous alcohol in the solvent. The exit line carrying the gaseous reaction mixture from the reactor is preferably well insulated to insure that the trialkoxysilane does not reflux. Refluxing can encourage the consecutive reaction of the trialkoxysilane with the alcohol, resulting in loss of the desired trialkoxysilane product by the formation of the tetraalkoxysilane.

The presence of gaseous alcohol, hydrogen gas and other gases in the reactor can occasionally lead to foaming. This is undesirable since it can result in loss of solvent, promoter and copper-activated silicon from the reactor. U.S. Pat. No. 5,783,720 discloses that the addition of foam control agents, preferably silicon-containing foam control agents such as OSi Specialties SAG® 1000, SAG® 100, SAG® 47, Wacker-Chemie OEL AF 98/300 and Dow Corning FS 1265, will negate or control this problem. SAG® 1000, SAG® 100 and SAG® 47 are compositions comprising polydimethyl-silicones and silica. FS 1265 and OEL AF 98/300 contain fluorinated silicones, for example, poly(trifluoropropylmethylsiloxanes). The foam control agent must be durable such that a single addition at the outset of a batch reaction is sufficient to avoid or mitigate foam formation until all of the silicon has been consumed.

At constant temperature, the reaction rate depends critically on the surface area and particle size of the silicon and copper catalyst precursor and on the feed rate of the alcohol. Higher reaction rates are obtained at higher surface areas, finer particle sizes and higher alcohol feed rates. These parameters are selected so that a safe, economically sustainable product output is realized without endangerment to people, property and the environment. Deactivation can be reduced or forestalled and stability sustained by reducing the alcohol flow during the course of the TES Direct Synthesis. This control not only decreases the excess alcohol available for dehydrogenation and other side reactions, it also facilitates product separation in the stripping column downstream of the reactor. The illustrated example will show that a steady-state profile is maintained beyond 60 percent, even beyond 70 percent, silicon conversion by reducing the alcohol flow rate 15-20 percent after about 40-50 percent silicon conversion and again after about 60-70 percent silicon conversion.

High selectivity to trialkoxysilanes, high reaction rates and stable performance are realized when nanosized copper catalyst precursors and cyano promoters are used in the present invention. This is particularly so when triethoxysilane is prepared by the Direct Synthesis process of the instant invention. Preferably, the nanosized copper catalyst precursor is prepared by reductive decomposition of high surface area copper (II) hydroxide in alkylated benzenes or cycloparaffins, as taught in the co-pending application (loc. cit.), and the cyano promoter is copper (I) cyanide, preferably nanosized copper (I) cyanide, or 1,6-dicyanohexane. Accordingly, in one embodiment of the invention, the triethoxysilane/tetraethoxysilane (TES/TEOS) ratio is at least about 10, and greater than about 15 in another embodiment, and in yet another embodiment greater than about 25.

In one embodiment of the invention, the silicon conversion is greater than about 40 percent, and greater than about 50 percent in another embodiment, before the reaction rate and/or selectivity to TES begins to decline monotonically. All of these advantages of the instant invention will be illustrated herein below by example.

Hydrogen is a co-product of the Direct Synthesis of trialkoxysilanes. Nitrogen is usually co-fed with the alcohol. The instant invention discloses that co-feeding carbon dioxide with the alcohol improves reaction stability of the cyanide and nitrile promoted Direct Synthesis.

In accordance with the present invention, substantial advantages are achieved in the Direct Synthesis of trialkoxysilanes by combined use of the nanosized copper catalyst precursors, particularly nanoparticulate copper (I) oxide, and cyanide or nitrile promoters. The most notable of these advantages is increased catalytic stability: the prolongation of reaction at desirable rates and selectivity. Additionally, the instant invention facilitates continuous and semi-batch manufacturing operation. In semi-batch operation, additional silicon is added to the slurry after 50-80 percent of the previous charge has been consumed and reaction is continued with the alcohol.

EXAMPLES

The following Examples illustrate the preferred embodiments of the instant invention. These are not intended to limit the scope of the invention. Rather, they are presented merely to facilitate the practice of the invention by those of ordinary skill in the art.

Table A contains a list of abbreviations used in the presentation of the data of the examples disclosed herein below.

TABLE A

| ABBREVIATION | MEANING |
| --- | --- |
| TMS | $HSi(OCH_3)_3$ (Trimethoxysilane) |
| TMOS | $Si(OCH_3)_4$ (Tetramethoxysilane) |
| MeOH | $CH_3OH$ (methanol) |
| TES | $HSi(OC_2H_5)_3$ (Triethoxysilane) |

TABLE A-continued

| ABBREVIATION | MEANING |
| --- | --- |
| TEOS | $Si(OC_2H_5)_4$ (Tetraethoxysilane) |
| SEL | $HSi(OR)_3/Si(OR)_4$ |
| % Si/hr | Percent silicon converted per hour |
| N 600 L | NALKYLENE ® 600 L (linear alkylbenzene, avg. mol. Wt. = 260 g/mol Sasol NA Inc. |
| N 550 BL | NALKYLENE ® 550 BL (linear alkylbenzene, avg. mol. Wt. = 243-244 g/mol) Sasol NA Inc. |
| TH59 | THERMINOL ® 59 (heat transfer fluid ethyl diphenyl ethane/diphenyl ethane/diethyl diphenyl ethane/ethylbenzene polymer) Available from Solutia Inc. |
| MLTHM | MARLOTHERM ® S (mixture of isomeric dibenzylbenzenes) Available from Hüls AG |
| mL | Milliliter |
| psig | Pounds per square inch gauge |
| N 500 | NALKYLENE ® 500 (1-phenyldodecane) Available from Sasol NA Inc. |
| g | gram |
| kg | kilogram |
| L | liter |
| nm | nanometer |
| μ | micron |
| $m^2/g$ | square meters per gram |
| rpm | revolutions per minute |
| wt % | weight percent |
| min | minute |
| s | second |
| STY | Space time yield, kg/kg · hr |
| Conv | Conversion |
| barg | Bar gauge |

Equipment Used

Stainless Steel Slurry Reactors A and B: A 5.8 liter CHEMINEER® reactor (Reactor A) was used for some of the Examples presented herein. Four 90° spaced, 1.27 cm wide baffles were affixed to the wall of the reactor. Agitation was provided by two impellers attached to an axial shaft. The bottom one was a six-blade Rushton turbine, 6.35 cm in diameter. A three-blade marine propeller of the same diameter was placed 10 cm above the turbine. A variable speed air-driven motor, whose rotational speed was measured by a magnetic tachometer, supplied power for agitation. An electric heating mantle controlled by a heater/temperature controller was used to heat the reactor.

Methanol or ethanol was supplied to the reactor from a 1 L storage container via a calibrated FMI laboratory pump. Coiled stainless steel tubing, 0.32 cm internal diameter×305 cm length, placed in a 4 L silicone oil bath controlled at 150° C. served as the alcohol vaporizer. A similar vaporizer coil was available for the recycle stream, but it was not used during the course of these experiments. The alcohol inlet line entered through the top of the reactor. It was heat traced to prevent condensation of the vapor. Alcohol vapor was injected 2.5 cm from the bottom of the reactor and below the level of the six-blade turbine through a single downward pointing (0.63 cm internal diameter) sparger. A pressure gauge attached the alcohol vapor inlet line gave higher readings (up to about 2 atmospheres) when the sparger was plugged. Ordinarily, the gauge was at zero. Additional alcohol was supplied to the storage container during an experiment to maintain an uninterrupted flow of this reagent.

Reaction products and unreacted alcohol exited the reactor through a 91.4 cm×2.54 cm internal diameter packed tube, which served as entrainment separator and partial distillation column to remove solvent and higher boiling silicates from the product stream. The packing was ceramic saddles and stainless steel mesh. Five thermocouples were distributed along the length of the tube to record temperatures and indicate foaming. The lowest thermocouple was flush with the top of the reactor. As was indicated hereinabove, foaming was controlled by the use of FS 1265, SAG® 47 and SAG® 100. Flexible tubing connected the outlet of the entrainment separator/partial distillation column to the four-way valve regulating sampling and crude product flow to the distillation columns.

Two ten plate Oldershaw distillation columns served to separate the liquid reaction products and unreacted alcohol from the gases. Effluent from the reactor was admitted into the top trays of the lower column, which was attached to a 3 neck 2 L round bottom flask supported in a heating mantle. A magnetically controlled reflux condenser and distillation head with thermocouple capped the upper column. The reflux condenser and another condenser downstream were cooled to −25° C. by circulating silicone oil. Uncondensed gases exited the condenser through a vapor lock bubbler into the hood. Wider tubing was employed downstream of the bubbler to avoid backpressures likely to shatter the glassware (columns, condensers and bubbler) or cause leaks at the joints. A gas sampling port was provided at a T joint downstream of the bubbler. Effluent gas flow was diluted with nitrogen prior to its discharge into the laboratory hood. A thermocouple was located in the second opening of the three-neck flask and the intake to an FMI laboratory pump in the other. The pump was used to transfer liquid product from the flask to Teflon coated polyethylene storage bottles. All glass containers used to store or sample trimethoxysilane and triethoxysilane were washed with dilute HCl, rinsed thoroughly with methanol (or ethanol) and oven dried at 110° C. prior to use.

Reactor B was of similar design to Reactor A. Its capacity was 8 liter. A larger alcohol reservoir was used. The same pumps, alcohol evaporator and product condensation equipment was used as described above for Reactor A. An assortment of impellers with different shapes, diameters and power numbers was available for use with the three reactors.

Glass Slurry Reactor (Reactor C): A 2.0 liter glass reactor was also used to illustrate the method and process of the present invention. Agitation was most often provided by two pitched, glass blades attached to an axial shaft, which was also of glass. The bottom blade was 5.7 cm in diameter and the top 3.9 cm. The blades were separated by 3.8 cm. A Model BDC 1850 Stirrer (Caframo Limited, Ontario, Canada) with digital speed control was the power source for agitation. An electric heating mantle controlled by a digital heater/temperature was used to heat the reactor.

Methanol or ethanol was supplied to the reactor from a 1 L calibrated addition funnel via a calibrated FMI pump. The alcohol was vaporized 130-160° C. by transit through a 30 cm long×0.32 cm diameter coiled, stainless steel tube placed in a silicone oil bath. Stainless steel tubing from the oil bath to the reactor inlet was also controlled at 130-160° C. with electrical heating tape.

Reaction products and unreacted alcohol exited the reactor through a 40 cm long×2.5 cm diameter Vigreux column controlled at 100° C. This served as an entrainment separator for solvent droplets. The gaseous reaction mixture was then admitted to a condenser, cooled to ~0° C. with chilled silicone oil, before it was collected in a sampling flask attached to a dry ice-isopropanol cold finger. Gas leaving the collection flask was cooled in second dry ice-isopropanol cold finger before being vented to the hood through a vapor lock bubbler. The bubbler contained silicone oil and had extra opening for the release of overpressure.

Gas chromatographic analysis of the reaction product was performed as described above.

General Copper-Silicon Activation and Reaction Procedure

Typically, the reactor was charged with solvent, silicon, copper catalyst precursor and foam control agent and then sealed. The solvent to silicon ratio was typically 2:1 or 4:1. The slurry was agitated at 700-900 rpm and nitrogen introduced during heating to the desired reaction temperature. Simultaneously, the alcohol vaporizer and feed inlet were heated to 150-170° C. and the refrigerant circulated through the reflux condenser was cooled to ~−25° C. Alcohol flow to the reactor was initiated when all the set temperatures were attained. Nitrogen (or another auxiliary gas, $H_2$, $CO_2$) flow was maintained during the reaction.

Once the alcohol flow was underway, sampling and analysis of the vent gas stream for hydrogen were done every 10-30 minutes until a stable composition was established. That indicated the end of the induction period. Thereafter, gas sampling was done every 30 minutes to monitor hydrogen and other uncondensed byproducts. During the course of the reaction, total vent gas flow was used as an approximate measure of the reaction rate according to the stoichiometry of equation (1).

Samples were collected in previously acid washed, alcohol rinsed, oven-dried containers attached at the four-way sampling valve for 2-5 minutes every half hour. The containers were cooled in dry-ice during sample collection. Samples were weighed and analyzed by gas chromatography (GC). The bulk of the liquid product was condensed in the three-neck flask, which served as the reboiler and transferred to storage. All of these data were used to calculate the temporal composition of the product stream, its selectivity to trialkoxysilane, the reaction rate and overall silicon conversion. Usually, reactions were terminated after >85% of the silicon charged to the reactor had been reacted. In some cases, terminations were made at lower and higher silicon conversions depending on the objective of the experiment. Residual solids from the reaction were sometimes recovered and weighed to calculate silicon conversion.

Gas samples were analyzed for hydrogen, nitrogen and hydrocarbon (e.g. methane, ethane) content on a Hewlett Packard 5840 gas chromatograph fitted with a GS-Molesieve 30 m×0.53 mm internal diameter (J & W Scientific, Folsom, Calif.) capillary column and flame ionization detector. Argon was the carrier gas. Gas chromatography-mass spectrometry (MS) was used to analyze for dimethyl ether. Liquid samples containing alkoxysilanes were analyzed on a Hewlett Packard 5890 gas chromatograph fitted with a 3.66 m×3.18 mm internal diameter stainless steel 20% OV-101 on 60/80 mesh Chromosorb WHP column (Supelco Inc., Bellafonte, Pa.) and thermal conductivity detector. Helium was the carrier gas. Data are reported in the Examples below only for the principal products, $HSi(OR)_3$ and $Si(OR)_4$ (R=methyl, ethyl). Byproducts such as $RSiH(OR)_2$ and $RSi(OR)_3$ were also formed, but at low concentrations.

Materials Used

Technical grade silicon samples utilized in the experiments of the illustrative Examples are identified in Table 1 along with relevant analytical data. In each case, particles in the size range, 45-300 micrometers, accounted for approximately 70 weight percent of the silicon. MARLOTHERM®S, NALKYLENE® 550 BL, NALKYLENE® 500 and THERMINOL® 59 were the solvents used. FS 1265 (Dow Corning) and SAG® 47 were the foam control agents. KOCIDE® Cu(OH)$_2$ (57-59 wt % Cu) with bulk density, 171-229 kg/m$^3$, surface area, 30-40 m$^2$/g, and particle size of 3-5 microns was used where indicated.

Composition of silicon samples used in the Comparative Examples and Examples of the invention are presented in Table 1.

TABLE 1

| Element | Sample Si-I | Sample Si-II |
|---|---|---|
| Al, wt % | 0.2 | 0.08 |
| Ba, ppm | 13.4 | <3 |
| Ca, ppm | 517 | 600 |
| Cr, ppm | 28.6 | 58.9 |
| Cu, ppm | 19.5 | 34.8 |
| Fe, wt % | 0.39 | 0.38 |
| Mg, ppm | 23.9 | 8.8 |
| Mn, ppm | 125 | 90.4 |

TABLE 1-continued

| Element | Sample Si-I | Sample Si-II |
|---|---|---|
| Ni, ppm | <10 | 15.5 |
| P, ppm | 25 | 26.8 |
| Pb, ppm | <10 | <10 |
| Sn, ppm | <10 | <10 |
| Ti, ppm | 312 | 299 |
| V, ppm | 20.5 | 14.3 |
| Zn, ppm | 6.6 | <5 |
| Zr, ppm | 100 | 29 |

Comparative Examples 1A-1C illustrate the poor reaction stability observed with the Direct Synthesis of triethoxysilane at 220-250° C. when Cu(OH)$_2$ is the catalyst precursor. Results of Comparative Example 1D for the trimethoxysilane Direct Synthesis at 250° C. are displayed in Table 2.

Raw materials and reaction conditions employed are summarized in Table 2. The reactions were run in Reactor A. Silicon and KOCIDE® Cu(OH)$_2$ were stirred and heated in the solvents at 240-250° C. for 1 hour prior to alcohol introduction. Nitrogen (0.8 L/min) was injected during the activation and reaction with the alcohols.

In the experiments of Comparative Examples 1A-1C, reaction with ethanol could not be sustained beyond 20% silicon conversion. Following an early peak in TES formation (40-44 wt % TES in product mixture), product formation declined sharply and finally stopped at less than 20 percent silicon conversion. Silicon conversion improved as reaction temperature was decreased from 250° C. to 220° C. Experiments similar to Comparative Example 1C with other Cu(OH)$_2$ lots gave peak TES 60-70 wt % at ~10% silicon conversion. However, stable catalysis could not be established. GC/MS analysis of the reaction mixtures in Examples 1A-1C revealed acetaldehyde (CH$_3$CHO) and acetal (CH$_3$CH(OC$_2$H$_5$)$_2$) during the period of decline. Formation of these by-products is believed to occur as depicted above in Equations 9 and 10.

Data for Direct Synthesis of TES and TMS with Cu(OH)$_2$ as catalyst precursor are displayed in Table 2.

TABLE 2

| Parameter | Comparative Example 1A | Comparative Example 1B | Comparative Example 1C | Comparative Example 1D |
|---|---|---|---|---|
| KOCIDE ® Cu(OH)$_2$, g | 14 | 11 | 11.67 | 7.05 |
| SOLVENT, g | N 550 BL 2000 | MLTHM 2000 | T59, 2070.2 | T59, 2093.7 |
| FS1265, g | 1.8 | 1.8 | 1.8 | 1.8 |
| SAG ® 47, g | — | 0.86 | 0.86 | — |
| Silicon (Si-II), g | 1000 | 1000 | 563.7 | 1000.3 |
| Cu Concentration, % | 0.82 | 0.64 | 1.20 | 0.41 |
| Temperature, ° C. | 250 | 230 | 220 | 250 |
| Agitation Rate, rpm | 900 | 900 | 800 | 800 |
| Alcohol Flow, g/min | C$_2$H$_5$OH, 5.0 | C$_2$H$_5$OH, 5.0 | C$_2$H$_5$OH, 4.8 | CH$_3$OH, 5.05 |
| Average Rate, % Si/hr | Not Determined | Not Determined | 2.67 | 6.13 |
| Silicon Conversion, % | 4 | 4 | 17.34 | 90.58 |
| TES Yield, g | Not Determined | Not Determined | 553.14 | 3755.68 (TMS) |
| TEOS Yield, g | Not Determined | Not Determined | 23.65 | 196.67 (TMOS) |
| Selectivity | Not Determined | Not Determined | 23.39 | 19.10 |

In contrast, the Direct Synthesis of trimethoxysilane proceeded to high silicon conversion (>90%) at 250° C. in Therminol® 59. The experiment of Comparative Example 1D continued for 14.78 hr. A stable steady-state was established at 85-88% TMS between 15-66% silicon conversion.

Comparative Examples 2A-2D illustrate that the Direct Synthesis of triethoxysilane improves when nanosized copper (I) oxide is the source of catalytic copper and the reaction temperature is 190-220° C.

Data for Direct Synthesis of TES with 515-4235 ppm Cu from nanosized Cu$_2$O are displayed in Table 3.

TABLE 3

| Parameter | Comparative Example 2A | Comparative Example 2B | Comparative Example 2C | Comparative Example 2D |
|---|---|---|---|---|
| Nano $Cu_2O$, g | 0.329 | 0.470 | 1.317 | 2.700 |
| NALKYLENE® 550 BL, g | 2022.6 | | 2008.2 | 2104.2 |
| Nalkylene® 500 | | 2020.5 | | |
| FS1265, g | 1.5 | 3.14 | 1.5 | 1.5 |
| SAG® 47, g | 0.8 | 1.61 | 0.8 | |
| Silicon (Si-II), g | 567.6 | 566.7 | 569.2 | 566.2 |
| Cu Concentration, ppm | 515 | 737 | 2055 | 4235 |
| Temperature, °C. | 195.1 ± 0.9 | 202.3 ± 0.8 | 204.5 ± 7.3 | 218.9 ± 3.2 |
| Agitation Rate, rpm | 900 | 900 | 900 | 900 |
| Ethanol Flow, g/min | 10.1 | 10.1 | 10.1 | 10.1 |
| Average Rate, % Si/hr | 6.04 | 6.46 | 13.32 | 13.63 |
| Silicon Conversion, % | 39.28 | 40.67 | 39.95 | 39.93 |
| TES Yield, g | 1242.38 | 1323.83 | 1301.71 | 1289.12 |
| TEOS Yield, g | 78.32 | 30.97 | 35.87 | 42.13 |
| Selectivity | 15.86 | 42.75 | 36.29 | 30.60 |
| Final Silicon Conversion, % | 46.23 | 48.34 | 55.89 | 48.95 |
| TES Yield, g | 1434.05 | 1572.81 | 1821.43 | 1581.13 |
| TEOS Yield, g | 127.97 | 37.53 | 49.87 | 50.81 |
| Final Selectivity | 11.21 | 41.91 | 36.52 | 31.12 |

For the experiments of Comparative Examples 2A, 2C and 2D, KOCIDE® $Cu(OH)_2$ (58.49 wt % Cu) was decomposed to nanosized $Cu_2O$ in NALKYLENE® 550BL at 250° C. for 1 hr as described in Example 1B of the co-pending application (loc. cit.). NALKYLENE® 500 was used in Comparative Example 2B. The weights used and the experimental data are given in Table 3. Nanosized $Cu_2O$ and the excess alkylated benzene solvent were added to the CHEMINEER® reactor along with the other raw materials shown in Table 3.

Note that Direct Synthesis of triethoxysilane was done in NALKYLENE® 550BL in Comparative Examples 2A, 2C and 2D and in NALKYLENE® 500 in Comparative Example 2B.

The reactions are compared at ~40% silicon conversion, since they were not all run to the same extent. The high activity of the nanosized $Cu_2O$ is evident in Comparative Examples 2A and 2B. Average reaction rates were 6-6.5% Si/hr at ~200° C. with the use of 500-750 ppm copper. Selectivity to TES was also very good. Copper concentrations in the range 2000-4250 ppm (Comparative Examples 2C and 2D) afforded higher reaction rates without loss of selectivity to TES. In Comparative Example 2A, maximum TES concentration (37.24 wt %) in the crude product was observed at 7.51 percent silicon conversion. At 46.23 percent silicon conversion, TES was only 13.40 wt % in the sample. Selectivity and rate improved in Comparative Example 2B wherein the usage of nanosized $Cu_2O$ was increased. Maximum TES was 39.04 wt % and the final sample, at 48.34 percent silicon conversion, contained only 7.11 wt % TES. In Comparative Example 2C, the maximum in TES formation was 73.18 wt % at 6.93 percent silicon conversion. TES formation decreased to 16.11 wt % at 55.89 percent silicon conversion. These values were altered somewhat when the copper concentration was increased in Comparative Example 2D. Maximum TES was 77.66 wt % at 8.34 percent silicon conversion and at 48.95 percent conversion, TES in the sample was 40.96 wt %.

These data show a consistent peak and drop-off of selectivity to TES when nanosized $Cu_2O$ is the source of catalytic copper. There is no steady-state region. The trends across Comparative Examples 2A-2D, taken together with the results of Comparative Example 1C, indicate that Direct TES reaction stability is better at 190-220° C. than at higher temperatures in the solvents studied. The results suggest that severe catalytic deactivation occurring >220° C. might be the source of the reduced silicon conversion at higher temperatures.

Comparative Examples 3A-3H: These Comparative Examples illustrate the absence of a stable steady-state in the Direct Synthesis of triethoxysilane with nanosized copper (I) oxide as the source of catalytic copper.

Reactor B was used. Comparative Example 3A-3H were performed at 200° C., 800 rpm with 3200 g NALKYLENE® 500, 10.1 g FS1265 and 4.1 g SAG® 47. Nanosized $Cu_2O$ was prepared by thermal decomposition of KOCIDE® $Cu(OH)_2$ in NALKYLENE® 500 as described in the co-pending application (loc. cit.). The amounts of raw materials and other experimental conditions are summarized in Table 4.

FIG. 1 presents a plot of wt % TES versus silicon conversion (reaction time) for the Comparative Example 3B. It is observed that a peak occurs in TES formation between 5 and 12 percent silicon conversion followed by a slow decline. There is no period during which TES remained relatively constant. This peaked profile characteristic of deactivation occurs under the wide range of copper concentrations and ethanol flow rates employed in the experiments Raw materials for the preparation of Comparative Examples 3A-3H are presented in Table 4.

TABLE 4

| | $Cu(OH)_2$, g | SILICON, g | ETHANOL, g/min | DURATION, hr |
|---|---|---|---|---|
| 3A | 1.85 | 1300 | 16.5 | 8 |
| 3B | 16 | 1600 | 12.0 | 16 |
| 3C | 16.2 | 1600 | 12.0 | 17 |
| 3D | 20.0 | 1600 | 12.0 | 15 |
| 3E | 16.0 | 1600 | 15.0 | 10 |
| 3F | 9.0 | 1600 | 12.0 | 15 |
| 3G | 9.0 | 1600 | 12.0 | 15 |
| 3H | 16.0 | 1600 | 8.0 | 16 |

Data for Comparative Examples 3A-3E experiments are summarized in Table 5. It is observed that TES content of the crude product was in the range 91-98 wt % and TEOS was 1-5 wt %. Comparison of the reaction rates (STY, kg crude/kg Si. hr) for Comparative Examples 3B and 3E, and 3C and 3D suggests that ethanol flow rate has a stronger influence on rate than does copper concentration.

Data for Direct TES Synthesis with different amounts of nanosized $Cu_2O$ and athanol flow rates (TES and TEOS weight percent in product shown in parentheses) is presented in Table 5.

TABLE 5

|  | Comparative Example 3A | Comparative Example 3B | Comparative Example 3C | Comparative Example 3D | Comparative Example 3E |
|---|---|---|---|---|---|
| Nano $Cu_2O$, g | 1.19 | 10.27 | 10.40 | 12.84 | 10.27 |
| Si (Si-I), g | 1300 | 1600 | 1600 | 1600 | 1600 |
| Ethanol, g/min | 16.5 | 12 | 12 | 12 | 15 |
| Duration, hr | 8 | 16 | 17 | 15 | 10 |
| TES Yield, g | 3245.53 (97.59%) | 7947.55 (93.76%) | 8123.61 (91.83%) | 7745.36 (94.39%) | 5647.00 (93.41%) |
| TEOS Yield, g | 44.02 (1.32%) | 404.49 (4.77%) | 441.25 (4.99%) | 326.14 (3.97%) | 246.42 (4.08%) |
| Selectivity | 73.73 | 19.65 | 18.41 | 23.75 | 22.92 |
| Si Conv., % | 43.6 | 89.72 | 92.90 | 87.01 | 63.77 |
| STY, kg/kg · hr | 0.320 | 0.331 | 0.325 | 0.342 | 0.378 |
| Maximum TES, wt % | 65.83 | 76.0 | 79.6 | 80.5 | 75.6 |
| Slope of $r/r_0$ Plot | −0.0447 | −0.0361 | −0.041 | −0.036 | −0.048 |
| Deactivation, % Si Conversion | >10 | >12 | >12 | >9 | >10 |

Example 4B of the instant invention is illustrative of the improvement in reaction stability (increase in silicon conversion) realized when CuCN is used in the Direct Synthesis of triethoxysilane.

Reactor C, with the same set and arrangement of impellers, was used for experiments utilizing Comparative Example 4A and Example 4B. The experiment of Comparative Example 4A was the comparative control. In both cases, 0.70 g $Cu(OH)_2$ was thermally decomposed to nanosized $Cu_2O$ (0.449 g) in 250 g Nalkylene® 500 in the reactor at 250° C. Thereafter, the mixture was cooled, and silicon (250 g Si-II), foam control agent (3.8 g FS 1265 300 cSt and 1.3 g SAG® 47) and 750 g additional Nalkylene® 500 were charged to the reactor. The temperature was then raised to 205° C. as the mixture was sparged with nitrogen and stirred at 800 rpm. CuCN (1.0 g) was added to the reaction of Example 4B at the outset. Ethanol vapor (4.1 g/min) was introduced at 205° C. and flow was continued for 8.0 hours in 4A and 10.42 hours in 4B.

The effect of CuCN on Direct TES Synthesis is displayed in Table 6.

TABLE 6

|  | Comparative Example 4A | Example 4B |
|---|---|---|
| CuCN, g | 0 | 1.0 |
| REACTION TIME, hr | 8.0 | 10.42 |
| TES YIELD, g | 695.16 | 861.41 |
| TEOS YIELD, g | 25.91 | 31.93 |
| SELECTIVITY | 26.83 | 26.97 |
| Si CONVERSION, % | 48.94 | 70.61 |
| MAXIMUM TES, wt % | 51.75 at 4.1% Si conv. | 58.64 at 13.44% Si conv. |

TABLE 6-continued

|  | Comparative Example 4A | Example 4B |
|---|---|---|
| FINAL TES, wt % | 14.08 | 19.10 |
| DEACTIVATION EQUATION, $r/r_0$ = | −0.1029 t + 1.00 $R^2$ = 0.9818 | −0.0837 t + 1.00 $R^2$ = 0.9822 |

Reactions were terminated when the TES content of the reaction product was below about 15-20 weight percent. The results are summarized in Table 6.

The data show that overall desirable performance was sustained in the reaction of Example 4B for 10.42 hours. The use of 4000 ppm CuCN (based on silicon charged) maintained average selectivity ~27, afforded average rate of 6.78% Si conversion/hr and increased silicon conversion by at least 44 percent over the control reaction of Comparative Example 4A, in which the average rate was 6.12% Si conversion/hr. The reduced slope (−0.0837) of the deactivation equation in Example 4B compared to that of Comparative Example 4A (−0.1029) demonstrates the flatter reaction profile and enhanced reaction stability that result from the use of CuCN in Example 4B.

Comparative Examples 5A and 5D and Examples 5B and 5C illustrate the effectiveness of 1000-2500 ppm CuCN in promoting the stability of the Direct Synthesis of triethoxysilane. They also demonstrate that CuCN is a bona fide promoter and does not itself activate silicon for reaction with ethanol.

Summary of the experimental data from Examples 5A-5D are displayed in Table 7.

TABLE 7

| Parameter | Comparative Example 5A | Example 5B | Example 5C | Comparative Example 5D |
|---|---|---|---|---|
| Nano $Cu_2O$, g | 0.458 | 0.449 | 0.450 | 0 |
| CuCN, g | 0 | 0.59 | 1.20 | 0.64 |
| NALKYLENE ®, g | 2020.5 | 2026.4 | 2027.9 | 2027.1 |
| FS1265, g | 3.14 | 3.20 | 3.39 | 3.12 |
| SAG 47, g | 1.61 | 1.46 | 1.50 | 1.50 |
| Silicon (Si-II), g | 566.7 | 560.6 | 566.2 | 573.9 |
| Temperature, ° C. | 201.8 ± 0.9 | 203.7 ± 1.1 | 206.1 ± 1.5 | 201.0 ± 0.5 |
| Ethanol, g/min | 10.1 | 10.1 | 10.1 | 10.1 |
| Duration, hr | 9.02 | 6.13 | 7.75 | 4 |
| TES Yield, g | 1572.81 | 2196.72 | 3099.77 | 0 |
| TEOS Yield, g | 37.53 | 61.83 | 113.82 | 0 |
| Selectivity | 41.91 | 35.82 | 27.23 | — |
| Si Conversion, % | 48.34 | 68.47 | 96.31 | — |
| TES Plateau, wt % | 38.48 ± 0.4, 4-13.1% Si conversion | 62.61 ± 1.18, 4-31% Si conversion | 62.18 ± 8.4, 6-79% Si conversion | — |
| Maximum TES, wt % | 39.04 at 13.1% Si conv. | 64.32 at 11.7% Si conv. | 79.29 at 42.0% Si conv. | — |
| Slope of $r/r_0$ Plot | −0.1283 | −0.0995 | −0.2322 | — |
| Si Conv. for $r/r_0$ Plot | 20-48.34 | 31-68.47 | 79-96.31 | — |

The experiments for Comparative Example 5A and 5D and Examples 5B-5C were performed in Reactor A using the raw material quantities and reaction conditions set forth in Table 7 and the procedure described in Comparative Example 4A and 4B above. Temperature was set at 200° C., agitation rate at 800 rpm and ethanol feed rate at 10.1 g/min. Modest exotherms in Examples 5B and 5C led to slightly higher average temperatures compared to the controls (Comparative Examples 5A and 5D).

The experiments were not all run to the same extent. Comparative Example 5A was terminated after ~9 hours. TES and TEOS in the reactor effluent at that time were then 7.11 wt % and 0.26 wt %, respectively. Example 5B was stopped after ~6 hours with TES at 41.30 wt % and TEOS at 1.42 wt % of the reactor effluent. Example 5C was continued for 7.75 hours. TES was 35.57 wt % and TEOS 0.97 wt % of the reaction product at that point. Comparative Example 5D showed no evidence of $H_2$, TES or TEOS formation after 4 hours. It was then terminated.

Comparison of the results of Comparative Examples 5A and 5D shows that the copper present in CuCN is not available for silicon activation. The initial copper concentration was 731 ppm in the slurry of Comparative Example 5A and 791 ppm in Comparative Example 5D. Thus, CuCN is not a catalyst precursor for the Direct Synthesis of triethoxysilane. However, the presence of 1052 ppm CuCN (Example 5B) and 2119 ppm CuCN (Example 5C) in reactions activated by nanosized $Cu_2O$ effected significant improvements in reaction rate and stability, while maintaining desirable selectivity. By comparing the duration and silicon conversion for Comparative Examples 5A, and Examples 5B-5C, it is observed that the average rate was 5.36% Si/hr, 11.17% Si/hr and 12.43% Si/hr, respectively, as CuCN usage was increased. Likewise, there was an extension of the TES plateau region and the maximum TES formation occurred farther along the reaction profile. Both of these reflect increased silicon conversion (higher reaction stability) with 1000-2500 ppm CuCN usage based on silicon.

Note that deactivation occurred later along the reaction profile as CuCN usage was increased. Deactivation was less severe in Example 5B compared with Comparative Example 5A. However, although deactivation occurred later in Example 5C, it was quite rapid.

Examples 6A-6D illustrate the beneficial effects of both carbon dioxide usage and control of ethanol flow on the CuCN promoter-enhanced stability of the Direct Synthesis of triethoxysilane with nanosized copper (I) oxide.

Reactor C was used with the reaction conditions and raw material quantities set forth in Tables 7A and 7B.

Description of experiments of Examples 6A-6D are displayed in Table 7A.

TABLE 7A

| Experiment | Conditions |
|---|---|
| Example 6A | Baseline experiment with CuCN and $CO_2$. Compare with $N_2$ data. |
| Example 6B | As in Example A, but with additional nano $Cu_2O$ after ~42% Si conversion |
| Example 6C | As in Example A, but with additional nano $Cu_2O$ and CuCN after ~55% Si conversion. 18 hr delay prior to restart ethanol flow |
| Example 6D | As in Example C with immediate restart of ethanol flow (~47% Si) |

The data show that the use of both carbon dioxide and CuCN afforded silicon conversions greater than 88%, selectivity greater than 20 and flat reaction profiles to 60-68% silicon conversion. Addition of more nano $Cu_2O$, i.e., Example 6B, was beneficial to reaction rate and stability. Note the lowering of the slope of the $r/r_0$ plot in Example 6B compared to Example 6A. Addition of both nano $Cu_2O$ and CuCN during the course of the TES Direct Synthesis (Examples 6C and 6D) decreased deactivation (note slopes) and contributed to increased selectivity to TES and to the sustenance of stable reaction.

Reaction conditions and results for Examples 6A-6D are displayed in Table 7B.

TABLE 7B

|  | Example 6A | Example 6B | Example 6C | Example 6D |
| --- | --- | --- | --- | --- |
| Nano Cu$_2$O, g | 0.223 | 0.223 (initial) 0.117 (later) | 0.223 (initial) 0.117 (later) | 0.223 (initial) 0.117 (later) |
| CuCN, g | 1.005 | 1.006 | 1.007 (initial) 1.005 (later) | 1.001 (initial) 1.006 (later) |
| N 500, g | 1008.7 | 1006.7 | 1002.4 | 1007.9 |
| FS1265, g | 3.31 | 3.22 | 3.28 | 3.22 |
| SAG 47, g | 1.30 | 1.31 | 1.48 | 1.45 |
| Si (Si-II), g | 253.0 | 255.4 | 253.6 | 257.0 |
| Temp, °C. | 205.1 ± 0.2 | 206.0 ± 2.1 | 206.5 ± 1.3 | 205.4 ± 1.2 |
| CO$_2$, L/min | 0.98 | 0.98 | 0.98 | 0.98 |
| Ethanol, g/min | 4.11 | 4.11 | 4.11 | 4.11 |
| Duration, hr | 11.10 | 10.47 | 10.22 | 10.67 |
| TES Yield, g | 1282.90 | 1273.47 | 1322.19 | 1332.29 |
| TEOS Yield, g | 50.28 | 60.31 | 43.81 | 35.68 |
| Selectivity | 25.52 | 21.11 | 30.18 | 37.34 |
| Si Conv., % | 89.36 | 88.42 | 91.46 | 90.50 |
| kg Crude/kg Si, hr | 0.475 | 0.499 | 0.527 | 0.499 |
| TES Plateau, wt % | 51.47 ± 0.91 between 8.15-41.06% Si | 50.78 ± 2.87 between 8.51-60.71% Si | 51.52 ± 4.92 between 7.53-67.79% Si | 51.94 ± 3.86 between 9-65.87% Si |
| Maximum TES, wt % | 53.24 at 13.24% Si Conv | 57.49 at 48.43% Si Conv | 56.97 at 10.86% Si Conv | 57.24 at 14.41% Si Conv |
| Slope of r/r$_0$ Plot | −0.1463 | −0.1229 | −0.1172 | −0.1086 |
| Si Conv. for r/r$_0$ Plot | 70.3-89.36 | 60.71-88.42 | 67.79-91.46 | 65.87-90.50 |

Examples 7A-7D illustrate the beneficial effects of control of ethanol flow on the CuCN-enhanced stability of the Direct Synthesis of triethoxysilane.

Reactor C was used at 205° C. with the other reaction conditions and raw material quantities set forth in Tables 8A and 8B.

Description of experiments of examples 7A-7D are displayed in Table 8A.

TABLE 8A

| Example 7A | Direct TES Synthesis with 4.11 g/min ethanol and 0.98 L/min CO$_2$ |
| --- | --- |
| Example 7B | As in Example A, but with reduced ethanol flow (3.38 g/min) after ~46% Si conversion. |
| Example 7C | Direct TES Synthesis with 4.11 g/min ethanol and 0.8 L/min N$_2$ |
| Example 7D | As in Example 6C, but with two ethanol flow reductions, 3.48 g/min and 2.90 g/min, after ~50 and ~60% Si conversion, respectively. |

The reaction conditions and results for examples 7A-7D are displayed in Table 8B.

TABLE 8B

|  | Example 7A | Example 7B | Example 7C | Example 7D |
| --- | --- | --- | --- | --- |
| Nano Cu$_2$O, g | 0.223 | 0.225 | 0.216 | 0.227 |
| CuCN, g | 1.005 | 1.002 | 1.001 | 1.004 |
| N 500, g | 1008.7 | 997.4 | 1004.7 | 977.4 |
| FS1265, g | 3.31 | 3.26 | 3.31 | 3.49 |
| SAG 47, g | 1.30 | 1.35 | 1.20 | 1.61 |
| Si (Si-II), g | 253.0 | 254.6 | 256.8 | 256.3 |
| Gas | CO$_2$, 0.98 L/min | CO$_2$, 0.98 L/min | N$_2$, 0.8 L/min | N$_2$, 0.8 L/min |
| Ethanol, g/min | 4.11 | 4.11 (initial) 3.38 (>46% Si) | 4.11 | 4.09 (initial) 3.48 (>50% Si) 2.90 (>60% Si) |
| Duration, hr | 11.10 | 11.20 | 8.5 | 11.87 |
| TES Yield, g | 1282.90 | 1256.19 | 1218.19 | 1275.17 |
| TEOS Yield, g | 50.28 | 54.13 | 47.43 | 47.11 |
| Selectivity | 25.52 | 23.21 | 25.85 | 27.07 |
| Si Conv., % | 89.36 | 87.23 | 80.26 | 87.54 |
| STY, kg/kg · h | 0.475 | 0.459 | 0.580 | 0.435 |
| TES Steady-State, wt % | 51.47 ± 0.91 between 8.15-41.06% Si Conv | 47.90 ± 1.65 between 5-59% Si Conv | 61.49 ± 1.17 between 10.36-30.55% Si Conv | 46.59 ± 1.75 between 5.22-67.46% Si Conv |

TABLE 8B-continued

|  | Example 7A | Example 7B | Example 7C | Example 7D |
|---|---|---|---|---|
| Maximum TES, wt % | 53.24 at 13.24% Si Conv | 50.19 at 16.58% Si Conv | 62.39 at 18.49% Si Conv | 49.58 at 32.08% Si Conv |
| Slope of $r/r_0$ Plot | −0.1463 | −0.0685 | −0.077 | −0.0611 |

In Example 7A, the steady-state period was 8-41 percent silicon conversion. Reduction of ethanol flow after 46 percent silicon conversion in Example 7B allowed extension of the steady-state to 59 percent silicon conversion. The slope of the deactivation plot in Example 7A was −0.1463 and in Example 7B it was −0.0685. This index of reaction stability was improved by 53 percent.

Steady-state extended from 10 to 31 percent silicon conversion in Example 7C. Control of ethanol flow caused extension to 68 percent silicon conversion in Example 7D. Deactivation was apparent only beyond 70 percent silicon conversion whereas in Example 7C, it was already evident at 40 percent silicon conversion. The slope of the deactivation plot in Example 7D was about 21 percent less than in Example 7C. Thus, the use of CuCN, when combined with control of ethanol flow, improves the stability of the TES Direct Synthesis.

Examples 8A-8D illustrate the cyanide-promoted and organonitrile-promoted Direct Synthesis of TES in THERMINOL® 59.

Reactor B was used for the experiments of Examples 8A-8D. 3.7 kg THERMINOL® 59, 1.6 kg silicon (Si-II) and 4.1 g FS1265 were used in each of Example 8A-8D. 4.1 g SAG® 47 was also used in Example 8A. Dodecanenitrile ($CH_3(CH_2)_{10}CN$, 1.5 g) was added along with CuCN to the experiment of Example 8D. All reactions were done at 200° C. Experimental details and the results are set forth in Table 9 below.

Reaction conditions and results for Examples 8A-8D are displayed in Table 9 (weight percentages shown in parentheses).

tained until 71% Si conversion. TES concentration in the final sample (92.1% Si conversion) was 65.58 wt %. Example 8C illustrates the flat reaction profile (see FIG. 1) and stable performance realized with CuCN as a promoter. Maximum TES (74.86 wt %) occurred at 37.9% Si conversion. At termination (87.52% Si conversion), TES was 48.46 wt % in the reactor effluent. Comparison of Examples 8A and 8D shows that a combination of CuCN and an organonitrile effected about a 30 percent increase in rate (space time yield). Maximum TES (84.52 wt %) in Example 8D occurred at 39.6% Si conversion. At termination (98.24% Si conversion), the final sample contained 60.62 wt % TES.

The data in Table 9 show that a stable steady-state was established in all of the experiments between 5 and 10 percent silicon conversion and that it lasted beyond 50 percent silicon conversion in all cases. TES concentration in the crude reaction product at steady-state was 70-80 weight percent and selectivity spanned 20-78. Silicon conversions exceeded 85 percent and were greater than 90 percent in some cases. All of these CuCN— and/or organonitrile—promoted Direct TES Synthesis experiments in Therminol® 59 exhibited desirable stability.

Example 9C and Comparative Examples 9A-9B illustrate the improvement in Direct TES reaction stability and overall catalytic performance when "dry process" CuCl is dissolved in an organic nitrile and then used as the catalyst precursor.

Example 9C and Comparative Examples 9A-9B were preformed in Reactor C at 220° C. with 4.12 g/min ethanol flow. Each experiment employed 250 g silicon (Si-I), 1 kg TH-59, 0.4 g SAG® 47 and 2.5 g "dry process" CuCl. CuCl was added as a powdered solid to Comparative Examples 9A and

TABLE 9

|  | Example 8A | Example 8B | Example 8C | Example 8D |
|---|---|---|---|---|
| Nano $Cu_2O$, g | 13.0 | 10.27 | 13.0 | 13.0 |
| CuCN, g | 3.0 | 6.4 | 3.0 | 3.0 |
| T59, g | 3200 | 3200 | 3200 | 3200 |
| Ethanol, g/min | 12 | 12 | 15 | 12 |
| Duration, hr | 20 | 18 | 16 | 15 |
| DES, g | 5.58, (0.06%) | 3.04, (0.03%) | 6.84, (0.08%) | 4.54, (0.05%) |
| ETDES, g | 133.18, (1.40%) | 118.81, (1.23%) | 106.58, (1.30%) | 97.82, (1.06%) |
| TES, g | 9098.15, (95.86%) | 9140.47, (94.77%) | 7968.33, (97.15%) | 8750.34, (94.41%) |
| ETES, g | 11.55, (0.12%) | 14.83, (0.15%) | 7.67, (0.09%) | 13.72, (0.15%) |
| TEOS, g | 233.14, (2.46%) | 357.16, (3.70%) | 103.31, (1.26%) | 393.98, (4.25%) |
| HVS, g | 9.76, (0.10%) | 10.11, (0.10%) | 8.95, (0.11%) | 8.33, (0.09%) |
| Selectivity | 39.02 | 25.59 | 77.13 | 22.21 |
| Si Conv., % | 89.71 | 92.13 | 87.52 | 98.24 |
| STY, kg/kg · hr | 0.297 | 0.335 | 0.320 | 0.386 |
| TES Steady-State, wt % | 69.74 ± 3.19 between 5-55.5% Si Conversion | 74.86 ± 3.97 between 7-71% Si Conversion | 72.05 ± 1.97 between 5-64% Si Conversion | 79.44 ± 5.76 between 10-74% Si Conversion. |

In Example 8A, the maximum (76.11 wt %) in the TES profile occurred at 55.5 percent silicon conversion. At termination (89.7% Si conversion), TES in the reactor effluent was 40 wt %. Example 8B exhibited its TES maximum (79.40 wt %) at 30.4% Si conversion, but stable performance was main- 9B, but was first dissolved in 25 mL $CH_3CN$ before use in Example 9C. CuCl+Si activation was at 240° C. for 1 hour in Comparative Examples 9A and 9C, and 12 hours in Example 9B. $CH_3CN$ (boiling point 82° C.) evaporated from the reactor before the onset of the CuCl+Si reaction and subsequent reaction with ethanol in Example 9C. The results are summarized in Table 10 below.

In Comparative Example 9A, deactivation of TES Direct Synthesis ensued after 28 percent silicon conversion. Steady-state TES was 49.01±0.71 wt %. The experiment was terminated when TES concentration of the reactor effluent declined to 17.28 wt %. Reaction performance improved in Comparative Example 9B when the CuCl+Si were heated 12 hours prior to ethanol introduction. Steady-state lasted to 65 percent silicon conversion and the steady-state TES was 51.84±1.30 wt %. At termination, TES concentration in the reactor effluent was 28.99 wt %. In contrast, the use of a $CH_3CN$ solution of "dry process" CuCl in Example 9C enabled only 1 hour CuCl+Si pre-heating prior to ethanol introduction. Deactivation of TES Direct Synthesis was delayed until after 64 percent silicon conversion. Steady-state TES was 53.35±1.80 wt %. At the end, TES concentration in the reactor effluent was 30 wt %. Overall, the reaction was more stable than the corresponding Comparative Example 9A. The data of Comparative Example 9B show that, in the absence of a nitrile, 12 hours of activation were required to match the performance of Example 9C.

Summary for experiments of Comparative Examples 9A and 9B and Example 9C is displayed in Table 10.

Ethanol flow rate was 12 g/min. Other details and the results are set forth in Table 11 below.

Comparative Example 10A showed peak TES formation (76.01 wt %) at about 12 wt % silicon conversion. Thereafter, TES concentration in the reaction product declined steadily until the reaction was discontinued at 89.72 wt % silicon conversion. Examples 10B-10E show that use of the organonitriles delayed the onset of deactivation until after about 40-50 percent silicon conversion. Steady-state was observed between about 10 to about 50 percent silicon conversion. The flatter reaction profiles of example 10B-10E were realized with 450-850 ppm organonitrile (based on initial silicon charged). The reaction profile of Example 10B is presented in FIG. 1. Example 8C presents a marked difference from Example 3B as displayed in FIG. 1, and exemplifies the improved reaction stability that can be realized with the practice of the instant invention. As was already noted hereinabove, delayed deactivation can be more rapid than that shown by the Comparative Example.

Performance data summary for the experiments of Examples 10B-10E and Comparative Example 10A are displayed in Table 11 (TES and TEOS weight percentages shown in parentheses).

TABLE 11

|  | Comparative Example 10A | Example 10B | Example 10C | Example 10D | Example 10E |
|---|---|---|---|---|---|
| NITRILE | NONE | 1,6-$CN(CH_2)_6CN$ | 1,6-$CN(CH_2)_6CN$ | 1,4-$CN(CH_2)_4CN$ | 1,8-$CN(CH_2)_8CN$ |
| NITRILE, g | 0 | 0.8 | 1.33 | 0.75 | 0.75 |
| Duration, hr | 16 | 14 | 21 | 14 | 14 |
| Si Conv., % | 89.72 | 89.28 | 97.79 | 85.12 | 82.58 |
| TES Yield, g | 7947.55 (93.76%) | 7945.29 (94.18%) | 8776.39 (94.88%) | 7533.49 (93.38%) | 7443.09 (95.70%) |
| TEOS Yield, g | 404.49 (4.77%) | 397.36 (4.71%) | 319.36 (3.45%) | 424.01 (5.26%) | 258.32 (3.32%) |
| Selectivity | 19.65 | 19.99 | 27.48 | 17.77 | 28.87 |
| STY, kg/kg · hr | 0.331 | 0.377 | 0.275 | 0.360 | 0.347 |
| Steady-State, % Si Conversion | none | 8-40 | 10-44 | 11-36 | 8-53 |
| Maximum TES, wt % | 76.01 | 81.63 | 77.40 | 80.62 | 79.92 |
| Slope, $r/r_0$ Plot | −0.036 $R^2 = 0.9655$ | −0.054 $R^2 = 0.9411$ | −0.059 $R^2 = 0.9676$ | −0.0895 $R^2 = 0.9857$ | −0.2228 $R^2 = 0.9806$ |
| Deactivation, % Si Conversion | >12 | >43 | >44 | >41 | >58 |

TABLE 10

|  | Comparative Example 9A | Comparative Example 9B | Example 9C |
|---|---|---|---|
| Activation Time, hr | 1 | 12 | 1 |
| Reaction Time, hr | 8.08 | 10.25 | 9.17 |
| Total Si Conversion, % | 58.1 | 92.4 | 86.8 |
| TES Yield, g | 838.69 | 1294.87 | 1216.18 |
| TEOS Yield, g | 42.88 | 70.54 | 67.80 |
| Selectivity | 19.56 | 18.36 | 17.94 |
| STY, kg/kg · hr | 0.436 | 0.533 | 0.560 |
| Deactivation, % Si Conv | >28 | >65 | >64 |
| Deactivation Slope | −0.123 | −0.094 | −0.115 |

Comparative Example 10A and Examples 10B-10E illustrate the improved reaction stability realized with the use of the organonitriles, 1,4-dicyanobutane, 1,6-dicyanohexane and 1,8-dicyanooctane.

The experiments of Comparative Example 10A and Examples 10B-10E were performed in Reactor B at 200° C. with 1600 g silicon (Si-I), 3200 g NALKYLENE® 500, 10.27 g nanosized $CU_2O$, 10.1 g FS1265 and 4.1 g SAG® 47.

Examples 11A-11C illustrate the organonitrile-promoted Direct Synthesis of TES at super-atmospheric pressures.

Examples 11A-11C were performed in Reactor B. Pressure (10 psig or 0.68 barg) was applied by means of a back pressure control valve between the reactor outlet and the distillation columns. Each experiment of Examples 11A-11C was performed at 200° C. with 1600 g silicon (Si-II), 3200 g NALKYLENE® 500, 10.1 g FS1265, 4.1 g SAG® 47 and 12 g/min ethanol flow. $Cu(OH)_2$ was decomposed to nanosized $Cu_2O$ in NALKYLENE® 500 as described previously. Hydrogen was injected as the auxiliary gas in Examples 11A and 11B. Nitrogen (0.8 L/min) was applied in Example 11C. Additional details are summarized in Table 12.

The copper concentrations (based on silicon charged) in the slurries at the outset of the experiments were 0.57 wt % in Example 11A and 0.32 wt % in Examples 11B and 11C. The corresponding 1,6-dicyanohexane concentrations were 500 ppm, 469 ppm and 438 ppm, respectively. The data show that all three reactions exhibited observable steady-state behavior up to 54-56 percent silicon conversion. Pressure and $CN(CH_2)_6CN$ slowed the deactivation and allowed increased TES selectivity and reaction stability.

The data summary for the experiments utilizing Examples 11A-11C are displayed in Table 12.

TABLE 12

|  | Example 11A | Example 11B | Example 11C |
|---|---|---|---|
| Nano $Cu_2O$, g | 10.27 | 5.78 | 5.78 |
| $CN(CH_2)_6CN$, g | 0.8 | 0.75 | 0.7 |
| $H_2$, L/min | 1.8 | 1.8 | $N_2$ (0.8 L/min) |
| Duration, hr | 15 | 19 | 16 |
| $H_2Si(OC_2H_5)_2$, g | 3.88 (0.06%) | 2.32 (0.03%) | 3.47 (0.05%) |
| $C_2H_5SiH(OC_2H_5)_2$, g | 53.57 (0.80%) | 59.72 (0.72%) | 56.18 (0.75%) |
| $HSi(OC_2H_5)_3$, g | 6597.15 (98.13%) | 8123.37 (97.70%) | 7382.10 (98.71%) |
| $C_2H_5Si(OC_2H_5)_3$, g | 0.28 (~0%) | 0 | 0 |
| $Si(OC_2H_5)_4$, g | 58.88 (0.88%) | 113.95 (1.37%) | 35.03 (0.47%) |
| HVS, g | 9.27 (0.14%) | 15.56 (0.18%) | 2.00 (0.02%) |
| Selectivity | 112.05 | 71.29 | 210.74 |
| STY, kg/kg · hr | 0.280 | 0.274 | 0.292 |
| Steady-State, % Si | 13-56 | 12-55 | 7-54 |
| Si Conversion, % | 71.74 | 88.59 | 79.90 |
| Deactivation Slope | −0.128 | −0.108 | −0.062 |

(Values in parentheses are weight percentages of the ethoxysilanes)

While the invention has been described with reference to certain embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out the process of the invention but that the invention will include all embodiments falling within the scope of the appended claims.

The invention claimed is:

1. A process for the Direct Synthesis of trialkoxysilane comprising the steps of:
   a) forming a reaction mixture comprising a thermally stable solvent, silicon metal and a catalytically effective amount of a nanosized copper catalyst precursor;
   b) agitating and heating the reaction mixture to form copper-activated silicon therein; and,
   c) adding to the reaction mixture
      (i) an alcohol $R^1OH$ wherein $R^1$ is an alkyl group containing from 1 to 6 carbon atoms,
      (ii) a catalyst-promoting amount of at least one CN-containing promoter, wherein the promoter possesses the general formula $X-(CN)_n$ wherein X is a hydrocarbon group $R^2$ of valence n containing from 1 to 40 carbon atoms, and optionally, silicon and/or etheric oxygen, and n is an integer with the value of 1 to 4,
the alcohol reacting with the copper-activated silicon to provide trialkoxysilane $HSi(OR^{1-})_3$ wherein $R^1$ is as defined.

2. The process of claim 1 wherein the nanosized copper catalyst precursor is selected from the group consisting of nanosized copper, nanosized copper oxides, nanosized copper chlorides, other nanosized copper salts, and mixtures thereof.

3. The process of claim 2 wherein the nanosized copper catalyst precursor has diameters in the range from 1 nanometer ($10^{-9}$ meter) to 100 nanometer ($10^{-7}$ meter).

4. The process of claim 1 wherein the nanosized copper catalyst precursor is selected from the group comprising copper, copper (I) oxide, copper (II) oxide, copper (I) chloride, copper (II) chloride, copper (II) hydroxide, basic cupric oxide, basic copper carbonate, copper carboxylate, copper alkoxide and mixtures thereof.

5. The process of claim 1 wherein the mixture of step (b) is heated from 150° C. to 350° C.

6. The process of claim 1 wherein n is 1 and $R^2$ is monovalent hydrocarbon group of up to 10 carbon atoms.

7. The process of claim 6 wherein the promoter is at least one member selected from the group consisting of acetonitrile, t-butyl nitrile, cyclohexyl nitrile, benzonitrile, benzyl nitrile, and mixtures thereof.

8. The process of claim 1 wherein n is 1 and $R^2$ an etheric oxygen-containing group $R^3OR^4$ in which $R^3$ is a monovalent hydrocarbon group and $R^4$ is a divalent hydrocarbon group, there being up to about 40 carbon atoms total in the etheric oxygen-containing group.

9. The process of claim 1 wherein n is 2 and $R^2$ is an etheric oxygen-containing group $R^5OR^6$ in which $R^5$ and $R^6$ divalent hydrocarbon groups, there being up to about 40 carbon atoms total in the etheric oxygen-containing group.

10. The process of claim 1 wherein n is 1 and $R^2$ is

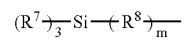

in which each $R^7$ is the same or different monovalent hydrocarbon group of up to about 12 carbon atoms, one or more of which optionally contain etheric oxygen, $R^8$ is a divalent hydrocarbon group of up to about 10 carbon atoms and m is 0 or 1.

11. The process of claim 10 wherein at least one $R^7$ is selected from the group consisting of methoxy, ethoxy and propoxy.

12. The process of claim 1 wherein n is 2 and $R^2$ is

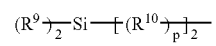

in which each $R^9$ is the same or different monovalent hydrocarbon group of up to about 12 carbon atoms, one or both of which optionally contain etheric oxygen, each $R^{10}$ is the same or different divalent hydrocarbon group of up to about 10 carbon atoms and p is 0 or 1.

13. The process of claim 12 wherein at least one $R^9$ is selected from the group consisting of methyl, ethyl and propyl.

14. The process of claim 1 wherein n is 3 and $R^2$ is

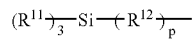

in which each $R^{11}$ is the same or different monovalent hydrocarbon group of up to about 12 carbon atoms, one or both of which optionally contain etheric oxygen, each $R^{12}$ is the same or different divalent hydrocarbon group of up to about 10 carbon atoms and p is 1.

15. The process of claim 14 wherein at least one $R^{11}$ is selected from the group consisting of methyl, ethyl and propyl.

16. The process of claim 1 wherein at least one promoter wherein X is hydrogen or a metal is combined with at least on promoter where X is $R^2$.

17. The process of claim 1 wherein the promoter is a catalyst-promoting amount of acetonitrile and CuCl.

18. The process of claim 9 wherein the promoter is selected from the group consisting of $CH_2(CN)_2$, 1,1-dicyanocyclohexane, 1,2-dicyanobenzene and 1,4-dicyanocyclohexane, and mixtures thereof.

19. The process of claim 14 wherein the promoter is selected from the group consisting of 2,4,6-tricyanotoluene, 1,3,5-tricyanobenzene, tricyanoethoxypropane, and mixtures thereof.

20. The process of claim 1 wherein the promoter is selected from the group consisting of 1,1,2,2-tetracyanoethane, 1,2,4,5-tetracyanobenzene, and 2,2,3,3-tetracyanoethylene oxide, and mixtures thereof.

21. The process of claim 1 wherein the promoter has a particle size from about 10 micrometers to about 0.1 nanometer.

22. The process of claim 21 wherein the promoter has a particle size that is less than about 1 micrometer.

23. The process of claim 16 wherein the promoter is a mixture of CuCN and $CH_3(CH_2)_{10}CN$.

24. The process of claim 16 wherein the promoter is a mixture of CuCN and $CN(CH_2)_6CN$.

25. The process of claim 1 wherein the promoter is present in an amount of about 100 parts per million to about 10 weight percent of the weight of silicon.

26. The process of claim 25 wherein the promoter is present in an amount from about 1000 parts per million to about 4 weight percent of the silicon.

27. The process of claim 5 wherein the promoter is present in an amount from about 100 parts per million to 6 weight percent of the silicon.

28. The process of claim 27 wherein the promoter is present in an amount from about 200 parts per million to about 4 weight percent of the silicon.

29. The process of claim 1 further comprising a foam control agent.

30. The process of claim 1 wherein the reaction temperature of step (c) is maintained at from 200° C. to 280° C.

31. The process of claim 1 wherein the silicon metal having a particle size of less than about 500 micron; one or more copper catalyst precursors having an average particle size from about 0.1 nm to about 600 nm, a surface area as low as 0.1 m²/g, in an amount from about 0.01 to about 5 parts by weight per 100 parts of said silicon metal such that about 0.008 to about 4.5 parts elemental copper is present based on 100 parts by weight of said silicon metal; the catalyst-promoting amount at least one promoter is from about 0.02 to about 6 parts by weight per 100 parts of said silicon metal; and a thermally stable reaction solvent present in an amount that provides a gravimetric ratio of solids to solvent of about 1:2 to about 1:4.

32. A trialkoxysilane produced by the process of claim 1.

33. A trialkoxysilane produced by the process of claim 1.

34. A trialkoxysilane produced by the process of claim 31.

35. A process for the Direct Synthesis of trialkoxysilane comprising the steps of:
 a) forming a reaction mixture comprising a thermally stable solvent, silicon metal and a catalytically effective amount of a copper catalyst precursor;
 b) agitating and heating the reaction mixture to form copper-activated silicon therein; and,
 c) adding the reaction mixture
  (i) an alcohol $R^1OH$ wherein $R^1$ is an alkyl group containing from 1 to 6 carbon atoms,
  (ii) a catalyst-promoting amount of at least one CN-containing promoter, wherein the promoter possesses the general formula X—$(CN)_n$ wherein X is a hydrocarbon group $R^2$ of valence n containing from 1 to 40 carbon atoms, and optionally, silicon and/or etheric oxygen, and n is an integer with the value of 1 to 4;
the alcohol reacting with the copper-activated silicon to provide trialkoxysilane $HSi(OR^1)_3$ wherein $R^1$ is defined.

36. A process for the Direct Synthesis of trialkoxysilane comprising the steps of:
 a) forming a reaction mixture comprising
  i) a thermally stable solvent in an amount that provides a gravimetric ratio of solids to solvent of about 1:2 to about 1:4,
  ii) silicon metal having a particle size of less than about 500 microns; and
  iii) a catalytically effective amount of a nanosized copper catalyst precursor having an average particle size from 0.1 nm to 600 nm and BET surface area of at least 0.1 m²/gram and in the amount from 0.01 to 5 parts by weight per 100 parts by weight a said silicon metal such that 0.008 to 4.5 parts elemental copper per 100 parts of said silicon metal;
 b) agitating and heating the reaction mixture to a temperature of between 190° C. to 350° to form nanosized copper catalysts precursor with an average particle size in the rang of from 1 nm to 100 nm which reacts with silicon metal to form a copper-activated silicon therein; and,
 c) adding to the reaction mixture maintained at a temperature from 190° C. to 240° C.
  i) an alcohol $R^1OH$ wherein $R^1$ is an alkyl group containing from 2 to 6 carbon atoms,
  ii) a catalyst-promoting amount of at least one CN-containing promoter, wherein the promoter possesses the general formula X—$(CN)_n$ wherein X is a hydrogen or a metal with a valence of n and n is an integer with the value of 1 to 4;
the alcohol reacting with the copper-activated silicon to provide trialkoxysilane $HSi(OR^1)_3$ wherein $R^1$ is defined.

37. The process of claim 35 wherein the CN-containing promoter is selected from the group consisting of HCN, LiCN, NaCN, KCN, $Ca(CN)_2$, $Mg(CN)_2$, and $Si(CN)_4$.

38. The process of claim 35 wherein the CN-containing promoter is selected from the group consisting of Cu(CN), $Pd(CN)_2$, Ag(CN) and $Ni(CN)_2$.

* * * * *